United States Patent [19]

Powers et al.

[11] Patent Number: 5,795,761
[45] Date of Patent: Aug. 18, 1998

[54] MUTANTS OF 2,5-DIKETO-D-GLUCONIC ACID (2,5-DKG) REDUCTASE A

[75] Inventors: David B. Powers, Somerset; Stephen Anderson, Princeton, both of N.J.

[73] Assignee: Rutgers, The State University of New Jersey, Piscatway, N.J.

[21] Appl. No.: 585,595

[22] Filed: Jan. 16, 1996

Related U.S. Application Data

[63] Continuation-in-part of Ser. No. 584,019, Jan. 11, 1996, abandoned.
[51] Int. Cl.$^6$ .............................. C12N 9/04; C12N 9/02; C12N 15/00; C12P 7/60
[52] U.S. Cl. .............. 435/190; 435/189; 435/69.1; 435/138; 435/172.1; 435/172.3; 435/843; 536/23.2
[58] Field of Search .................. 435/42, 69.1, 41, 435/71.2, 138, 172.1, 189, 190, 191, 320.1, 252.3, 252.32, 172.3, 843; 536/23.2

[56] References Cited

U.S. PATENT DOCUMENTS

| | | | |
|---|---|---|---|
| Re. 30,872 | 2/1982 | Sonoyama et al. | 435/138 |
| 3,959,076 | 5/1976 | Sonoyama et al. | 195/30 |
| 3,998,697 | 12/1976 | Sonoyama et al. | 195/30 |
| 4,543,331 | 9/1985 | Sonoyama et al. | 435/138 |
| 4,704,692 | 11/1987 | Ladner | 364/496 |
| 4,757,012 | 7/1988 | Estell et al. | 435/172.3 |
| 4,758,514 | 7/1988 | Light et al. | 435/91 |
| 4,760,025 | 7/1988 | Estell et al. | 435/222 |
| 4,853,871 | 8/1989 | Pantoliano et al. | 364/496 |
| 4,908,773 | 3/1990 | Pantoliano et al. | 364/496 |
| 4,945,052 | 7/1990 | Hardy et al. | 435/172.3 |
| 5,004,690 | 4/1991 | Light et al. | 435/138 |
| 5,008,193 | 4/1991 | Anderson et al. | 435/138 |
| 5,017,691 | 5/1991 | Lee et al. | 530/351 |
| 5,032,514 | 7/1991 | Anderson et al. | 435/138 |
| 5,376,544 | 12/1994 | Lazarus et al. | 435/190 |
| 5,583,025 | 12/1996 | Lazarus et al. | 435/190 |

FOREIGN PATENT DOCUMENTS

| | | | |
|---|---|---|---|
| 046284 | 8/1981 | European Pat. Off. | C12N 1/20 |
| 088409 | 3/1983 | European Pat. Off. | C12P 39/00 |
| 142169 | 11/1984 | European Pat. Off. | C12N 9/04 |

OTHER PUBLICATIONS

Anderson, S. et al., "Production of 2-Keto-L-Gulonate, an International in L-Ascorbate Synthesis, by a Genetically Modified *Erwinia herbicola*," *Science* 230: 144–149 (1985).

Bajorath, J. et al., "Review-Knowledge-Based Model Building of Proteins: Concepts and Examples," *Protein Science* 2: 1798–1810 (1993).

Bohr, H. et al., "Protein Secondary Structure And Homology by Neural Networks—The X-Helices in Rhodopsin," *FEBS Letters* 241(1.2) 223–228 (1988).

Bohren, K.M. et al., "The Aldo-Keto Reductase Superfamily," *The Journal of Biological Chemistry* 264(16) 9547–9551 (1989).

Borhani, D.W. et al., "The Crystal Structure of the Aldose Reductase—NADPH Binary Complex," *The Journal of Biological Chemistry* 267(34): 24841–24847 (1992).

Carper, D.A., et al., "A Superfamily of NADPH-dependent Reductases in Eukaryotes and Prokaryotes," *Experimental Eye Research* 49 377–388 (1989).

Deléage, G. et al., "An Algorithm For Protein Secondary Structure Prediction Based On Class Prediction," *Protein Engineering* 1(4): 289–294 (1987).

Farber, G.K. et al., "The Evolution of $\alpha\beta$ Barrel Enzymes," *Trends in Biochemical Sciences*, 15 228–235 (1990).

Fasman, G.D., "Protein Conformational Prediction," *Trends in Biochemical Sciences* 14: 295–299 (1989).

Greer, J., "Comparative Modeling of Homologous Proteins," *Methods in Enzymology* 202: 239–252 (1991).

Grindley, J.F. et al., "Conversion of Glucose to 2-Keto-L-Gulonate, an Intermediate in L-Ascorbate Synthesis by a Recombinant Strain of *Erwinia citreus*," *Appl. Environ. Microbial.* 54: 1770–1775 (1988).

Holley, L.H. et al., "Protein Secondary Structure Prediction With a Neural Network," *Proc. Nat'l. Acad. Sci. U.S.A.* 86: 152–156 (1988).

Hoog, S.S. et al., "Three-Dimensional Structure Of Rat Liver 3α-Hydroxysteroid/Dihydrodiol Dehydrogenase: A Member Of The Aldo-Keto Reductase Superfamily," *Proc. Nat'l. Acad. Sci. U.S.A.* 91: 2517–2521 (1994).

Imanaka, T. et al., "A New Way of Enhancing the Thermostability of Proteases," *Nature* 324: 695–697 (1986).

Kellis, J.T. et al., "Contribution of Hydrophobic Interactions to Protein Stability," *Nature* 333: 784–786 (1988).

Klein, P. et al., "Prediction Of Protein Structural Class From The Amino Acid Sequence," *Biopolymers* 25: 1659–1672 (1986).

Matsumura, M. et al., "Substantial Increase of Protein Stability by Multiple Disulphide Bonds," *Nature* 342: 291–293 (1989).

Matthews, B.W. et al., "Enhanced Protein Thermostability from Site-Directed Mutations that Decreases the Entropy of Unfolding," *Proc. Nat'l. Acad. Sci. (U.S.s.A.)* 84: 6663–6667 (1987).

Miller, J.V. et al., "Purification and Characterization of 2,5-Diketo-D-Gulonate Reductase from Corynebacterium Sp.," *J. Biol. Chem.* 269: 9016–9020 (1987).

(List continued on next page.)

*Primary Examiner*—Robert A. Wax
*Assistant Examiner*—Elizabeth Slobodyansky
*Attorney, Agent, or Firm*—Howry & Simon; Jeffrey I. Auerbach; Kevin W. McCabe

[57] ABSTRACT

Mutants of 2,5-diketo-D-gluconic acid reductase A an enzyme used to produce 2-keto-L-gluconic acid, a precursor of ascorbic acid (vitamin C), are prepared by site-directed mutagenesis. These mutants may exhibit one or more of the following characteristics: improved temperature stability, increased resistance to substrate inhibition, increased turnover of the substrate by the enzyme and increased affinity for the substrate.

12 Claims, 12 Drawing Sheets

OTHER PUBLICATIONS

Moult, J. et al., "An Algorithm For Determining The Conformation Of Polypeptide Segments In Proteins And Systematic Search," *Proteins: Structure, Functions and Genetics* 1: 146–163 (1986).

Nakashima, H. et al., "The Folding Type of a Protein is relevant to the amino acid composition," *The Journal of Biochemistry* 99(1): 153–162 (1986).

Nicholson, H. et al., "Enhanced Protein Thermostability from Designated Mutations that Interact with a α–Helix Dipoles," *Nature* 336: 651–656 (1988).

Qian, Ning et al., "Predicting The Secondary Structure Of Globular Proteins Using Neural Network Models," *J. Mol. Biol.* 202: 865–884 (1988).

Rasteller, W.H., "Enzyme Engineering: Applications and Promise," *Trends Biotechnol.* 1: 80–84 (1983).

Richardson, J.S. et al., "Amino Acid Preferences for Specific Locations at the Ends of a α–Helices," *Science* 240: 1648–1652 (1988).

Robson, B. et al., "Expert System For Protein Engineering: Its Application In The Study Of Chloramphenicol Acetyltransferase And Avian Pancreatic Polypeptide," *Journal Of Molecular Graphics* 5(1): 8–17 (1987).

Rondeau, J.M. et al., "Novel NADPH–Binding Domain Revealed By The Crystal Structure Of Aldose Reductase," *Nature—International Weekly Journal of Science* 355: 469–472 (1992).

Schulz, G.E. et al., "Principles of Protein Structure," (Springer Advanced Texts In Chemistry; 9th printing) pp. 170–175 (1991).

Sonoyama, T. et al., "Distribution of Microorganisms Capable of Reducing 2,5–Diketo–D–Gluconate to 2–Keto–L–Gluonate," *Agric. Biol. Chem.* 51: 2003–2004 (1987).

Sonoyama, T. et al., "Production of 2–Keto–L–Glucose by Two Stage Fermentation," *Appl. Environ. Microbiol.* 43: 1064–1069 (1982).

Sonoyama, T. et al., "Purification and Properties of Two 2,5 Diketo–D–Gluconate Reductases From a Mutant Strain Derived from Corynebacterium sp.," *J. Ferment Technol.* 65: 311–317 (1987).

vanGunsteren, W.F., "The Role Of Computer Simulation Techniques In Protein Engineering," *Protein Engineering* 2(1): 5–13 (1988).

Wells, J.A. et al., "Recruitment of Substrate–Specificity Properties from One Enzyme into a Related One by Protein Engineering," *Proc. Nat'l. Acad. Sci. (U.S.A.)* 84: 5167–5171 (1987).

Wilkinson, A.J. et al., "A Large Increase in Enzyme–Substrate Affinity by Protein Engineering," *Nature* 307: 187–188 (1984).

Wilson, D.K. et al., "An Unlikely Sugar Substrate Site In The 1.65A Structure Of The Human Aldose Reductase Holoenzyme Implicated In Diabetic Complications," *Science* 257: 81–84 (1992).

Wilson, D.K. et al., "Refined 1.8A Structure of Human Aldose Reductase Complexed With The Potent Inhibitor Zopolrestate," *Proc. Nat'l. Acad. Sci. U.S.A.* 90: 9847–9851 (1993).

Yang, M.M. et al., "In: Reaction Centers of Photosynthetic Bacteria," (Michael–Beyerle, Ed.), Springer–Verlag, Germany 209–218 (1990).

Arase et al (1993) FEBS 316:123–127 "Stabilization of xylanase by random mutagenesis".

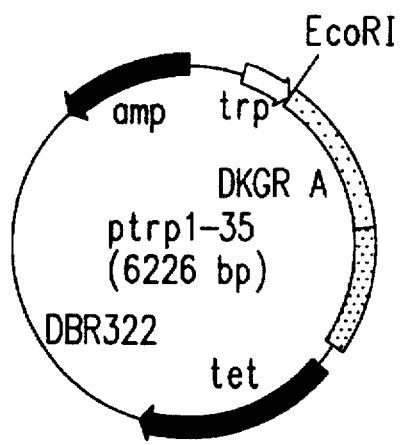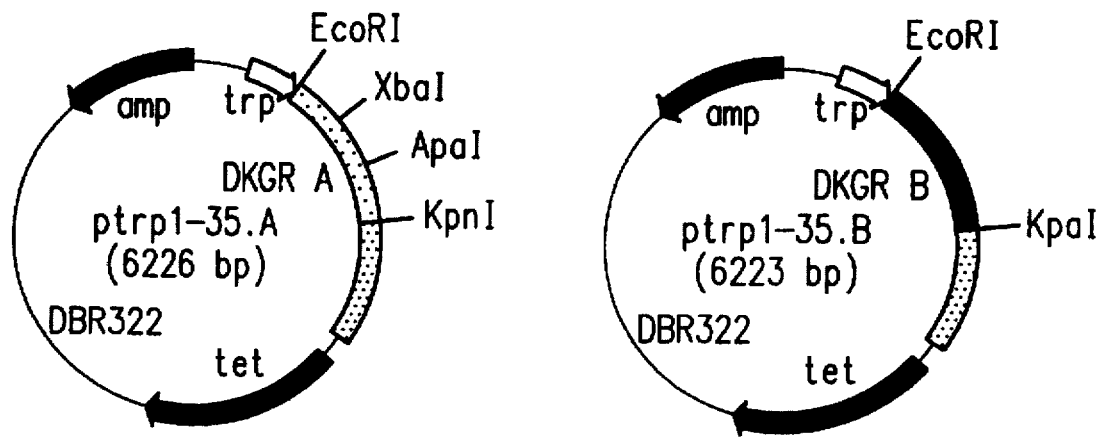
FIG.3

| ALGORITHMIC MODEL | | HOMOLOGY MODEL | | |
|---|---|---|---|---|
| COIL | 1-3 | COIL | 1-18 | |
| BETA | 4-8 | BETA | 19-20 | (β1) |
| COIL | 9-34 | COIL | 21-25 | |
| | | HELIX | 26-39 | (α1) |
| | | COIL | 40-42 | |
| BETA | 35-42 | BETA | 43-45 | (β2) |
| COIL | 43-53 | COIL | 46-52 | |
| HELIX | 54-60 | HELIX | 53-62 | (α2) |
| COIL | 61-69 | COIL | 63-70 | |
| BETA | 70-74 | BETA | 71-73 | (β3) |
| COIL | 75-85 | COIL | 74-85 | |
| HELIX | 86-93 | HELIX | 86-97 | (α3) |
| COIL | 94-103 | COIL | 98-103 | |
| BETA | 104-108 | BETA | 104-107 | (β4) |
| COIL | 109-118 | COIL | 108-116 | |
| HELIX | 119-128 | HELIX | 117-129 | (α4) |
| COIL | 129-131 | COIL | 130-135 | |
| BETA | 132-138 | BETA | 136-139 | (β5) |
| COIL | 139-142 | COIL | 140-142 | |
| HELIX | 143-150 | HELIX | 143-150 | (α5) |
| COIL | 151-158 | COIL | 151-158 | |
| BETA | 159-164 | BETA | 159-163 | (β6) |
| COIL | 165-168 | COIL | 164-170 | |
| HELIX | 169-177 | HELIX | 171-179 | (α6) |
| COIL | 178-181 | COIL | 180-182 | |
| BETA | 182-186 | BETA | 183-187 | (β7) |
| COIL | 187-198 | COIL | 188-200 | |
| HELIX | 199-209 | HELIX | 201-210 | (H1) |
| COIL | 210-215 | COIL | 211-213 | |
| BETA | 216-223 | HELIX | 214-223 | (α7) |
| COIL | 224-226 | COIL | 224-227 | |
| BETA | 227-230 | BETA | 228-229 | (β8) |
| COIL | 231-234 | COIL | 230-235 | |
| HELIX | 235-241 | HELIX | 236-243 | (α8) |
| COIL | 242-243 | | | |
| BETA | 244-250 | COIL | 244-251 | |
| COIL | 251-252 | | | |
| HELIX | 253-261 | HELIX | 252-259 | (H2) |
| COIL | 262-278 | COIL | 260-278 | |

FIG.5

```
              β₁              α₁                    β₂
.MTVPSIVLNDGNSIPQLG YG VFKVP PADTQRAVEEALEV GYRHID TAAI
MPNIPTISLNDGRPFPELG LG TYNLR GDEGVAAMVAAIDS GYRLLD TAVN
..MASRILLNNGAKMPILG LG TWKSP PGQVTEAVKVAIDV GYRHID CAHV

α₂                       β₃                α₃
YGN EEGVGAAI....AA SGIARDDL F IT TKLWNDRHGDE PAAAIAESLA
YEN ESEVGRAV....RA SSVDRDEL I VA SKLPGRQHGRAE AVDSIRGSLD
YQN ENEVGVAIQEKLRE QVVKREEL F IV SKLWCTYHEKGL VKGACQKTLS

β₄                                           α₄
KL ALDQVD LYLV HWPT................. PAADN YVHAWEKMIEL
RL GLDVID LQLI HWPN................. PSVGR WLDTWRGMIDA
DL KLDYLD LYLI HWPTGFKPGKEFFPLDESGNVVPSDTN ILDTWAAMEEL

β₅         α₅                    β₆             α₆
RA AGLTRS IGVS NHL VPHLERIV AATGV..VPA VNQIE LHPAYQQ REITD
RE AGLVRS IGVS NFT EPMLKTLI DETGV..TPA VNQVE LHPYFPQ AALRA
VD EGLVKA IGIS NFN HLQVEMIL NKPGLKYKPA VNQIE CHPYLTQ EKLIQ

β₇                          H1              α₇
WAAA HDVK IESW GPLG........QGKYDLFGA EPVTAAAAAH GKT PAQA
FHDE HGIR TESW SPLA........R.RSELLTE QLLQELAVVY GVT PTQV
YCQS KGIV VTAY SPLGSPDRPWAKPEDPSLLED PRIKAIAAKH NKT TAQV

β₈       α₈                  H2
VLRWHL QKGF VVF PKSVR RERLEENL DVFDFDLT DTEIAAID AMDPGD..
VLRWHV QLGS TPI PKSAD PDRQRENA DVFGFALT ADQVDAIS GLERGR..
LIRFPM QRNL VVI PKSVT PERIAENF KVFDFELS SQDMTTLL SYNRNWRV

......GSGRVSAHPDEVD    -DKGR A
......LWDGDPDTHEEM.    -DKGR B
CALLSCTSHKDYPFHEEF.    -ALDOSE REDUCTASE
```

FIG.6

| ENZYME | Km FOR NADPH (μM, +/- STD. ERR.) |
|---|---|
| DKGR A | 6.43 +/- 0.37 |
| DKGR B | 6.99 +/- 0.57 |
| F22Y | 7.07 +/- 0.75 |
| Q192R | 5.97 +/- 0.67 |
| A272G | 4.92 +/- 0.52 |
| F22Y/A272G | 8.19 +/- 1.15 |

FIG.11

| ENZYME | TM |
|---|---|
| DKGR A | 38 |
| DKGR B | 32 |
| F22Y | 41 |
| Q192R | 37 |
| A272G | 38 |
| F22Y/A272G | 40 |

FIG.12

SEQUENCE LISTING ( 1 ) GENERAL INFORMATION:

( i i i ) NUMBER OF SEQUENCES: 35

( 2 ) INFORMATION FOR SEQ ID NO:1:

( i ) SEQUENCE CHARACTERISTICS:
        ( A ) LENGTH: 278 amino acids
        ( B ) TYPE: amino acid
        ( D ) TOPOLOGY: linear ( i i ) MOLECULE TYPE: protein ( i i i ) HYPOTHETICAL: NO ( v i ) ORIGINAL SOURCE:
        ( A ) ORGANISM: 2,5 DKG REDUCTASE A
        ( C ) INDIVIDUAL ISOLATE: CORYNEBACTERIUM SP.

( x i ) SEQUENCE DESCRIPTION: SEQ ID NO:1:

```
Met  Thr  Val  Pro  Ser  Ile  Val  Leu  Asn  Asp  Gly  Asn  Ser  Ile  Pro  Gln
 1              5                        10                       15

Leu  Gly  Tyr  Gly  Val  Phe  Lys  Val  Pro  Pro  Ala  Asp  Thr  Gln  Arg  Ala
            20                        25                       30

Val  Glu  Glu  Ala  Leu  Glu  Val  Gly  Tyr  Arg  His  Ile  Asp  Thr  Ala  Ala
         35                       40                     45

Ile  Tyr  Gly  Asn  Glu  Glu  Gly  Val  Gly  Ala  Ala  Ile  Ala  Ala  Ser  Gly
     50                        55                       60
```

-continued

| | | | | | | | | | | | | | | |
|---|---|---|---|---|---|---|---|---|---|---|---|---|---|---|
| Ile | Ala | Arg | Asp | Asp | Leu | Phe | Ile | Thr | Thr | Lys | Leu | Trp | Asn | Asp | Arg |
| 65 | | | | | 70 | | | | | 75 | | | | | 80 |
| His | Asp | Gly | Asp | Glu | Pro | Ala | Ala | Ala | Ile | Ala | Glu | Ser | Leu | Ala | Lys |
| | | | | 85 | | | | | 90 | | | | | 95 | |
| Leu | Ala | Leu | Asp | Gln | Val | Asp | Leu | Tyr | Leu | Val | His | Trp | Pro | Thr | Pro |
| | | | 100 | | | | | 105 | | | | | 110 | | |
| Ala | Ala | Asp | Asn | Tyr | Val | His | Ala | Trp | Glu | Lys | Met | Ile | Glu | Leu | Arg |
| | | | 115 | | | | 120 | | | | | 125 | | | |
| Ala | Ala | Gly | Leu | Thr | Arg | Ser | Ile | Gly | Val | Ser | Asn | His | Leu | Val | Pro |
| | | 130 | | | | 135 | | | | | 140 | | | | |
| His | Leu | Glu | Arg | Ile | Val | Ala | Ala | Thr | Gly | Val | Val | Pro | Ala | Val | Asn |
| 145 | | | | | 150 | | | | | 155 | | | | | 160 |
| Gln | Ile | Glu | Leu | His | Pro | Ala | Tyr | Gln | Gln | Arg | Glu | Ile | Thr | Asp | Trp |
| | | | | 165 | | | | | 170 | | | | | 175 | |
| Ala | Ala | Ala | His | Asp | Val | Lys | Ile | Glu | Ser | Trp | Gly | Pro | Leu | Gly | Gln |
| | | | 180 | | | | | 185 | | | | | 190 | | |
| Gly | Lys | Tyr | Asp | Leu | Phe | Gly | Ala | Glu | Pro | Val | Thr | Ala | Ala | Ala | Ala |
| | | 195 | | | | | 200 | | | | | 205 | | | |
| Ala | His | Gly | Lys | Thr | Pro | Ala | Gln | Ala | Val | Leu | Arg | Trp | His | Leu | Gln |
| | 210 | | | | | 215 | | | | | 220 | | | | |
| Lys | Gly | Phe | Val | Val | Phe | Pro | Lys | Ser | Val | Arg | Arg | Glu | Arg | Leu | Glu |
| 225 | | | | | 230 | | | | | 235 | | | | | 240 |
| Glu | Asn | Leu | Asp | Val | Phe | Asp | Phe | Asp | Leu | Thr | Asp | Thr | Glu | Ile | Ala |
| | | | | 245 | | | | | 250 | | | | | 255 | |
| Ala | Ile | Asp | Ala | Met | Asp | Pro | Gly | Asp | Gly | Ser | Gly | Arg | Val | Ser | Ala |
| | | | 260 | | | | 265 | | | | | 270 | | | |
| His | Pro | Asp | Glu | Val | Asp | | | | | | | | | | |
| | | 275 | | | | | | | | | | | | | |

(2) INFORMATION FOR SEQ ID NO:2:

( i ) SEQUENCE CHARACTERISTICS:
        ( A ) LENGTH: 277 amino acids
        ( B ) TYPE: amino acid
        ( D ) TOPOLOGY: linear ( i i ) MOLECULE TYPE: protein ( i i i ) HYPOTHETICAL: NO ( v i ) ORIGINAL SOURCE:
        ( A ) ORGANISM: DKGR B
        ( B ) STRAIN: CORYNEBACTERIUM SP.

( x i ) SEQUENCE DESCRIPTION: SEQ ID NO:2:

| | | | | | | | | | | | | | | |
|---|---|---|---|---|---|---|---|---|---|---|---|---|---|---|---|
| Met | Pro | Asn | Ile | Pro | Thr | Ile | Ser | Leu | Asn | Asp | Gly | Arg | Pro | Phe | Pro |
| 1 | | | | 5 | | | | | 10 | | | | | 15 | |
| Glu | Leu | Gly | Leu | Gly | Thr | Tyr | Asn | Leu | Arg | Gly | Asp | Glu | Gly | Val | Ala |
| | | | 20 | | | | | 25 | | | | | 30 | | |
| Ala | Met | Val | Ala | Ala | Ile | Asp | Ser | Gly | Tyr | Arg | Leu | Leu | Asp | Thr | Ala |
| | | 35 | | | | | 40 | | | | | 45 | | | |
| Val | Asn | Tyr | Glu | Asn | Glu | Ser | Glu | Val | Gly | Arg | Ala | Val | Arg | Ala | Ser |
| | 50 | | | | | 55 | | | | | 60 | | | | |
| Ser | Val | Asp | Arg | Asp | Glu | Leu | Ile | Val | Ala | Ser | Lys | Leu | Pro | Gly | Arg |
| 65 | | | | | 70 | | | | | 75 | | | | | 80 |
| Gln | His | Gly | Arg | Ala | Glu | Ala | Val | Asp | Ser | Ile | Arg | Gly | Ser | Leu | Asp |
| | | | | 85 | | | | | 90 | | | | | 95 | |
| Arg | Leu | Gly | Leu | Asp | Val | Ile | Asp | Leu | Gln | Leu | Ile | His | Trp | Pro | Asn |
| | | | 100 | | | | | 105 | | | | | 110 | | |

```
Pro  Ser  Val  Gly  Arg  Trp  Leu  Asp  Thr  Trp  Arg  Gly  Met  Ile  Asp  Ala
          115                 120                      125

Arg  Glu  Ala  Gly  Leu  Val  Arg  Ser  Ile  Gly  Val  Ser  Asn  Phe  Thr  Glu
     130                      135                 140

Pro  Met  Leu  Lys  Thr  Leu  Ile  Asp  Glu  Thr  Gly  Val  Thr  Pro  Ala  Val
145                      150                 155                           160

Asn  Gln  Val  Glu  Leu  His  Pro  Tyr  Phe  Pro  Gln  Ala  Ala  Leu  Arg  Ala
               165                      170                           175

Phe  His  Asp  Glu  His  Gly  Ile  Arg  Thr  Glu  Ser  Trp  Ser  Pro  Leu  Ala
          180                      185                           190

Arg  Arg  Ser  Glu  Leu  Leu  Thr  Glu  Gln  Leu  Leu  Gln  Glu  Leu  Ala  Val
     195                      200                      205

Val  Tyr  Gly  Val  Thr  Pro  Thr  Gln  Val  Val  Leu  Arg  Trp  His  Val  Gln
     210                      215                      220

Leu  Gly  Ser  Thr  Pro  Ile  Pro  Lys  Ser  Ala  Asp  Pro  Asp  Arg  Gln  Arg
225                      230                      235                      240

Glu  Asn  Ala  Asp  Val  Phe  Gly  Phe  Ala  Leu  Thr  Ala  Asp  Gln  Val  Asp
               245                      250                      255

Ala  Ile  Ser  Gly  Leu  Glu  Arg  Gly  Arg  Leu  Trp  Asp  Gly  Asp  Pro  Asp
               260                      265                      270

Thr  His  Glu  Glu  Met
          275
```

( 2 ) INFORMATION FOR SEQ ID NO:3:

( i ) SEQUENCE CHARACTERISTICS:
        ( A ) LENGTH: 316 amino acids
        ( B ) TYPE: amino acid
        ( D ) TOPOLOGY: linear ( i i ) MOLECULE TYPE: protein ( i i i ) HYPOTHETICAL: NO ( v i ) ORIGINAL SOURCE:
        ( A ) ORGANISM: ALDOSE REDUCTASE
        ( B ) STRAIN: HOMO SAPIENS ( x i ) SEQUENCE DESCRIPTION: SEQ ID NO:3:

```
Met  Ala  Ser  Arg  Ile  Leu  Leu  Asn  Asn  Gly  Ala  Lys  Met  Pro  Ile  Leu
1                   5                      10                      15

Gly  Leu  Gly  Thr  Trp  Lys  Ser  Pro  Pro  Gly  Gln  Val  Thr  Glu  Ala  Val
          20                      25                      30

Lys  Val  Ala  Ile  Asp  Val  Gly  Tyr  Arg  His  Ile  Asp  Cys  Ala  His  Val
          35                      40                      45

Tyr  Gln  Asn  Glu  Asn  Glu  Val  Gly  Val  Ala  Ile  Gln  Glu  Lys  Leu  Arg
     50                      55                      60

Glu  Gln  Val  Val  Lys  Arg  Glu  Glu  Leu  Phe  Ile  Val  Ser  Lys  Leu  Trp
65                       70                      75                       80

Cys  Thr  Tyr  His  Glu  Lys  Gly  Leu  Val  Lys  Gly  Ala  Cys  Gln  Lys  Thr
               85                      90                      95

Leu  Ser  Asp  Leu  Lys  Leu  Asp  Tyr  Asp  Leu  Leu  Tyr  Leu  Ile  His  Trp
               100                     105                     110

Pro  Thr  Gly  Phe  Lys  Pro  Gly  Lys  Glu  Phe  Phe  Pro  Leu  Asp  Glu  Ser
          115                     120                     125

Gly  Asn  Val  Val  Pro  Ser  Asp  Thr  Asn  Ile  Leu  Asp  Thr  Trp  Ala  Ala
     130                     135                     140

Met  Glu  Glu  Leu  Val  Asp  Glu  Gly  Leu  Val  Lys  Ala  Ile  Gly  Ile  Ser
```

|     |     |     |     |     |     |     |     |     |     |     |     |     |     |     |     |
|---|---|---|---|---|---|---|---|---|---|---|---|---|---|---|---|
| 145 |  |  |  |  | 150 |  |  |  |  | 155 |  |  |  |  | 160 |

Asn Phe Asn His Leu Gln Val Glu Met Ile Leu Asn Lys Pro Gly Leu
          165                    170                175

Lys Tyr Lys Pro Ala Val Asn Gln Ile Glu Cys His Pro Tyr Leu Thr
            180              185              190

Gln Glu Lys Leu Ile Gln Tyr Cys Gln Ser Lys Gly Ile Val Val Thr
        195                200              205

Ala Tyr Ser Pro Leu Gly Ser Pro Asp Arg Pro Trp Ala Lys Pro Glu
    210              215              220

Asp Pro Ser Leu Leu Glu Asp Pro Arg Ile Lys Ala Ile Ala Ala Lys
225              230              235              240

His Asn Lys Thr Thr Ala Gln Val Leu Ile Arg Phe Pro Met Gln Arg
            245              250              255

Asn Leu Val Val Ile Pro Lys Ser Val Thr Pro Glu Arg Ile Ala Glu
        260              265              270

Asn Phe Lys Val Phe Asp Phe Glu Leu Ser Ser Gln Asp Met Thr Thr
        275              280              285

Leu Leu Ser Tyr Asn Arg Asn Trp Arg Val Cys Ala Leu Leu Ser Cys
    290              295              300

Thr Ser His Lys Asp Tyr Pro Phe His Glu Glu Phe
305              310              315

( 2 ) INFORMATION FOR SEQ ID NO:4:

( i ) SEQUENCE CHARACTERISTICS:
        ( A ) LENGTH: 28 base pairs
        ( B ) TYPE: nucleic acid
        ( C ) STRANDEDNESS: single
        ( D ) TOPOLOGY: linear ( i i ) MOLECULE TYPE: DNA (genomic)

( i i i ) HYPOTHETICAL: NO ( i v ) ANTI-SENSE: NO ( v i ) ORIGINAL SOURCE:
        ( A ) ORGANISM: CORYNEBACTERIUM SP ( x i ) SEQUENCE DESCRIPTION: SEQ ID NO:4:

CGCGAAGCTG GCTCTAGATC AGGTCGAC          28

( 2 ) INFORMATION FOR SEQ ID NO:5:

( i ) SEQUENCE CHARACTERISTICS:
        ( A ) LENGTH: 25 base pairs
        ( B ) TYPE: nucleic acid
        ( C ) STRANDEDNESS: single
        ( D ) TOPOLOGY: linear ( i i ) MOLECULE TYPE: DNA (genomic)

( i i i ) HYPOTHETICAL: NO ( i v ) ANTI-SENSE: NO ( v i ) ORIGINAL SOURCE:
        ( A ) ORGANISM: CORYNEBACTERIUM SP ( x i ) SEQUENCE DESCRIPTION: SEQ ID NO:5:

ATCGTGGGGG CCCCTCGGTC AGGGC          25

( 2 ) INFORMATION FOR SEQ ID NO:6:

( i ) SEQUENCE CHARACTERISTICS:

( A ) LENGTH: 28 base pairs
( B ) TYPE: nucleic acid
( C ) STRANDEDNESS: single
( D ) TOPOLOGY: linear ( i i ) MOLECULE TYPE: DNA (genomic)

( i i i ) HYPOTHETICAL: NO ( i v ) ANTI-SENSE: NO ( v i ) ORIGINAL SOURCE:
( A ) ORGANISM: CORYNEBACTERIUM SP ( x i ) SEQUENCE DESCRIPTION: SEQ ID NO:6:

GAGGTCGACT GAGGTACCCG AACACCCG       28

( 2 ) INFORMATION FOR SEQ ID NO:7:

( i ) SEQUENCE CHARACTERISTICS:
( A ) LENGTH: 24 base pairs
( B ) TYPE: nucleic acid
( C ) STRANDEDNESS: single
( D ) TOPOLOGY: linear ( i i ) MOLECULE TYPE: DNA (genomic)

( i i i ) HYPOTHETICAL: NO ( i v ) ANTI-SENSE: NO ( v i ) ORIGINAL SOURCE:
( A ) ORGANISM: CORYNEBACTERIUM SP ( x i ) SEQUENCE DESCRIPTION: SEQ ID NO:7:

GGGTATCTAG AATTCTATGC CGAA       24

( 2 ) INFORMATION FOR SEQ ID NO:8:

( i ) SEQUENCE CHARACTERISTICS:
( A ) LENGTH: 28 base pairs
( B ) TYPE: nucleic acid
( C ) STRANDEDNESS: single
( D ) TOPOLOGY: linear ( i i ) MOLECULE TYPE: DNA (genomic)

( i i i ) HYPOTHETICAL: NO ( i v ) ANTI-SENSE: NO ( v i ) ORIGINAL SOURCE:
( A ) ORGANISM: CORYNEBACTERIUM SP ( x i ) SEQUENCE DESCRIPTION: SEQ ID NO:8:

CGACCGGCTG GGTCTAGACG TGATCGAC       28

( 2 ) INFORMATION FOR SEQ ID NO:9:

( i ) SEQUENCE CHARACTERISTICS:
( A ) LENGTH: 30 base pairs
( B ) TYPE: nucleic acid
( C ) STRANDEDNESS: single
( D ) TOPOLOGY: linear ( i i ) MOLECULE TYPE: DNA (genomic)

( i i i ) HYPOTHETICAL: NO ( i v ) ANTI-SENSE: NO ( v i ) ORIGINAL SOURCE:
( A ) ORGANISM: CORYNEBACTERIUM ( x i ) SEQUENCE DESCRIPTION: SEQ ID NO:9:

ACCGAGAGCT GGGGGCCCCT CGCCCGGCGC                                              30

( 2 ) INFORMATION FOR SEQ ID NO:10:

( i ) SEQUENCE CHARACTERISTICS:
        ( A ) LENGTH: 30 base pairs
        ( B ) TYPE: nucleic acid
        ( C ) STRANDEDNESS: single
        ( D ) TOPOLOGY: linear ( i i ) MOLECULE TYPE: DNA (genomic)

( i i i ) HYPOTHETICAL: NO ( i v ) ANTI-SENSE: NO ( v i ) ORIGINAL SOURCE:
        ( A ) ORGANISM: CORYNEBACTERIUM SP ( x i ) SEQUENCE DESCRIPTION: SEQ ID NO:10:

GAAGAGATGT AGGGTACCGA TGCCGCGCAC                                              30

( 2 ) INFORMATION FOR SEQ ID NO:11:

( i ) SEQUENCE CHARACTERISTICS:
        ( A ) LENGTH: 18 base pairs
        ( B ) TYPE: nucleic acid
        ( C ) STRANDEDNESS: single
        ( D ) TOPOLOGY: linear ( i i ) MOLECULE TYPE: DNA (genomic)

( i i i ) HYPOTHETICAL: NO ( i v ) ANTI-SENSE: NO ( v i ) ORIGINAL SOURCE:
        ( A ) ORGANISM: CORYNEBACTERIUM SP ( x i ) SEQUENCE DESCRIPTION: SEQ ID NO:11:

TTCCCAGTCA CGACGTTG                                                           18

( 2 ) INFORMATION FOR SEQ ID NO:12:

( i ) SEQUENCE CHARACTERISTICS:
        ( A ) LENGTH: 28 base pairs
        ( B ) TYPE: nucleic acid
        ( C ) STRANDEDNESS: single
        ( D ) TOPOLOGY: linear ( i i ) MOLECULE TYPE: DNA (genomic)

( i i i ) HYPOTHETICAL: NO ( i v ) ANTI-SENSE: NO ( v i ) ORIGINAL SOURCE:
        ( A ) ORGANISM: CORYNEBACTERIUM SP ( x i ) SEQUENCE DESCRIPTION: SEQ ID NO:12:

CGCGAAGCTG GCTCTAGATC AGGTCGAC                                                28

( 2 ) INFORMATION FOR SEQ ID NO:13:

( i ) SEQUENCE CHARACTERISTICS:
        ( A ) LENGTH: 25 base pairs
        ( B ) TYPE: nucleic acid
        ( C ) STRANDEDNESS: single
        ( D ) TOPOLOGY: linear ( i i ) MOLECULE TYPE: DNA (genomic)

( i i i ) HYPOTHETICAL: NO ( i v ) ANTI-SENSE: NO ( v i ) ORIGINAL SOURCE:
    ( A ) ORGANISM: CORYNEBACTERIUM SP ( x i ) SEQUENCE DESCRIPTION: SEQ ID NO:13:

ATCGTGGGGG CCCCTCGGTC AGGGC     25

( 2 ) INFORMATION FOR SEQ ID NO:14:

( i ) SEQUENCE CHARACTERISTICS:
        ( A ) LENGTH: 28 base pairs
        ( B ) TYPE: nucleic acid
        ( C ) STRANDEDNESS: single
        ( D ) TOPOLOGY: linear ( i i ) MOLECULE TYPE: DNA (genomic)

( i i i ) HYPOTHETICAL: NO ( i v ) ANTI-SENSE: NO ( v i ) ORIGINAL SOURCE:
        ( A ) ORGANISM: CORYNEBACTERIUM SP ( x i ) SEQUENCE DESCRIPTION: SEQ ID NO:14:

GAGGTCGACT GAGGTACCCG AACACCCG     28

( 2 ) INFORMATION FOR SEQ ID NO:15:

( i ) SEQUENCE CHARACTERISTICS:
        ( A ) LENGTH: 23 base pairs
        ( B ) TYPE: nucleic acid
        ( C ) STRANDEDNESS: single
        ( D ) TOPOLOGY: linear ( i i ) MOLECULE TYPE: DNA (genomic)

( i i i ) HYPOTHETICAL: NO ( i v ) ANTI-SENSE: NO ( v i ) ORIGINAL SOURCE:
        ( A ) ORGANISM: CORYNEBACTERIUM SP ( x i ) SEQUENCE DESCRIPTION: SEQ ID NO:15:

GCCCCTCGGT CGCGGCAAGT ACG     23

( 2 ) INFORMATION FOR SEQ ID NO:16:

( i ) SEQUENCE CHARACTERISTICS:
        ( A ) LENGTH: 29 base pairs
        ( B ) TYPE: nucleic acid
        ( C ) STRANDEDNESS: single
        ( D ) TOPOLOGY: linear ( i i ) MOLECULE TYPE: DNA (genomic)

( i i i ) HYPOTHETICAL: NO ( i v ) ANTI-SENSE: NO ( v i ) ORIGINAL SOURCE:
        ( A ) ORGANISM: CORYNEBACTERIUM SP ( x i ) SEQUENCE DESCRIPTION: SEQ ID NO:16:

CGGGTACGGC GTCTACAAGG TGCCGCCGG     29

( 2 ) INFORMATION FOR SEQ ID NO:17:

-continued (i) SEQUENCE CHARACTERISTICS:
        (A) LENGTH: 17 base pairs
        (B) TYPE: nucleic acid
        (C) STRANDEDNESS: single
        (D) TOPOLOGY: linear (ii) MOLECULE TYPE: DNA (genomic)

(iii) HYPOTHETICAL: NO (iv) ANTI-SENSE: NO (vi) ORIGINAL SOURCE:
        (A) ORGANISM: CORYNEBACTERIUM SP (xi) SEQUENCE DESCRIPTION: SEQ ID NO:17:

CGGCGTCTAC AAGGTGC                                                            17

(2) INFORMATION FOR SEQ ID NO:18:

(i) SEQUENCE CHARACTERISTICS:
        (A) LENGTH: 29 base pairs
        (B) TYPE: nucleic acid
        (C) STRANDEDNESS: single
        (D) TOPOLOGY: linear (ii) MOLECULE TYPE: DNA (genomic)

(iii) HYPOTHETICAL: NO (iv) ANTI-SENSE: NO (vi) ORIGINAL SOURCE:
        (A) ORGANISM: CORYNEBACTERM SP (xi) SEQUENCE DESCRIPTION: SEQ ID NO:18:

TGGGCTCGGC ACGTTCAACC TGCGCGGCG                                               29

(2) INFORMATION FOR SEQ ID NO:19:

(i) SEQUENCE CHARACTERISTICS:
        (A) LENGTH: 17 base pairs
        (B) TYPE: nucleic acid
        (C) STRANDEDNESS: single
        (D) TOPOLOGY: linear (ii) MOLECULE TYPE: DNA (genomic)

(iii) HYPOTHETICAL: NO (iv) ANTI-SENSE: NO (vi) ORIGINAL SOURCE:
        (A) ORGANISM: CORYNEBACTERIUM SP (xi) SEQUENCE DESCRIPTION: SEQ ID NO:19:

CGGCACGTTC AACCTGC                                                            17

(2) INFORMATION FOR SEQ ID NO:20:

(i) SEQUENCE CHARACTERISTICS:
        (A) LENGTH: 29 base pairs
        (B) TYPE: nucleic acid
        (C) STRANDEDNESS: single
        (D) TOPOLOGY: linear (ii) MOLECULE TYPE: DNA (genomic)

(iii) HYPOTHETICAL: NO (iv) ANTI-SENSE: NO (vi) ORIGINAL SOURCE:

(A) ORGANISM: CORYNEBACTERIUM SP (x i) SEQUENCE DESCRIPTION: SEQ ID NO:20:

CGACACCGCG GCGAACTACG GAAACGAAG                    29

(2) INFORMATION FOR SEQ ID NO:21:

(i) SEQUENCE CHARACTERISTICS:
            (A) LENGTH: 17 base pairs
            (B) TYPE: nucleic acid
            (C) STRANDEDNESS: single
            (D) TOPOLOGY: linear (i i) MOLECULE TYPE: DNA (genomic)

(i i i) HYPOTHETICAL: NO (i v) ANTI-SENSE: NO (v i) ORIGINAL SOURCE:
            (A) ORGANISM: CORYNEBACTERIUM SP (x i) SEQUENCE DESCRIPTION: SEQ ID NO:21:

CGCGGCGAAC TACGGAA                                 17

(2) INFORMATION FOR SEQ ID NO:22:

(i) SEQUENCE CHARACTERISTICS:
            (A) LENGTH: 31 base pairs
            (B) TYPE: nucleic acid
            (C) STRANDEDNESS: single
            (D) TOPOLOGY: linear (i i) MOLECULE TYPE: DNA (genomic)

(i i i) HYPOTHETICAL: NO (i v) ANTI-SENSE: NO (v i) ORIGINAL SOURCE:
            (A) ORGANISM: CORYNEBACTERIUM SP (x i) SEQUENCE DESCRIPTION: SEQ ID NO:22:

TCGACACGGC GGTGGCGTAC GAGAACGAGA G                 31

(2) INFORMATION FOR SEQ ID NO:23:

(i) SEQUENCE CHARACTERISTICS:
            (A) LENGTH: 17 base pairs
            (B) TYPE: nucleic acid
            (C) STRANDEDNESS: single
            (D) TOPOLOGY: linear (i i) MOLECULE TYPE: DNA (genomic)

(i i i) HYPOTHETICAL: NO (i v) ANTI-SENSE: NO (v i) ORIGINAL SOURCE:
            (A) ORGANISM: CORYNEBACTERIUM SP (x i) SEQUENCE DESCRIPTION: SEQ ID NO:23:

GGCGGTGGCG TACGAGA                                 17

(2) INFORMATION FOR SEQ ID NO:24:

(i) SEQUENCE CHARACTERISTICS:
            (A) LENGTH: 22 base pairs
            (B) TYPE: nucleic acid
            (C) STRANDEDNESS: single
            (D) TOPOLOGY: linear ( i i ) MOLECULE TYPE: DNA (genomic)

( i i i ) HYPOTHETICAL: NO ( i v ) ANTI-SENSE: NO ( v i ) ORIGINAL SOURCE:
    ( A ) ORGANISM: CORYNEBACTERIUM SP ( x i ) SEQUENCE DESCRIPTION: SEQ ID NO:24:

GATGAGGTCG CGTGAGGTAC CC      22

( 2 ) INFORMATION FOR SEQ ID NO:25:

( i ) SEQUENCE CHARACTERISTICS:
        ( A ) LENGTH: 22 base pairs
        ( B ) TYPE: nucleic acid
        ( C ) STRANDEDNESS: single
        ( D ) TOPOLOGY: linear ( i i ) MOLECULE TYPE: DNA (genomic)

( i i i ) HYPOTHETICAL: NO ( i v ) ANTI-SENSE: NO ( v i ) ORIGINAL SOURCE:
        ( A ) ORGANISM: CORYNEBACTERIUM SP ( x i ) SEQUENCE DESCRIPTION: SEQ ID NO:25:

CCCGATGAGG CGGACTGAGG TA      22

( 2 ) INFORMATION FOR SEQ ID NO:26:

( i ) SEQUENCE CHARACTERISTICS:
        ( A ) LENGTH: 22 base pairs
        ( B ) TYPE: nucleic acid
        ( C ) STRANDEDNESS: single
        ( D ) TOPOLOGY: linear ( i i ) MOLECULE TYPE: DNA (genomic)

( i i i ) HYPOTHETICAL: NO ( i v ) ANTI-SENSE: NO ( v i ) ORIGINAL SOURCE:
        ( A ) ORGANISM: CORYNEBACTERIUM SP ( x i ) SEQUENCE DESCRIPTION: SEQ ID NO:26:

CACCCCGATG CCGTCGACTG AG      22

( 2 ) INFORMATION FOR SEQ ID NO:27:

( i ) SEQUENCE CHARACTERISTICS:
        ( A ) LENGTH: 22 base pairs
        ( B ) TYPE: nucleic acid
        ( C ) STRANDEDNESS: single
        ( D ) TOPOLOGY: linear ( i i ) MOLECULE TYPE: DNA (genomic)

( i i i ) HYPOTHETICAL: NO ( i v ) ANTI-SENSE: NO ( v i ) ORIGINAL SOURCE:
        ( A ) ORGANISM: CORYNEBACTERIUM SP ( x i ) SEQUENCE DESCRIPTION: SEQ ID NO:27:

GCACACCCCG CGGAGGTCGA CT      22

( 2 ) INFORMATION FOR SEQ ID NO:28:

( i ) SEQUENCE CHARACTERISTICS:
        ( A ) LENGTH: 23 base pairs
        ( B ) TYPE: nucleic acid
        ( C ) STRANDEDNESS: single
        ( D ) TOPOLOGY: linear ( i i ) MOLECULE TYPE: DNA (genomic)

( i i i ) HYPOTHETICAL: NO ( i v ) ANTI-SENSE: NO ( v i ) ORIGINAL SOURCE:
        ( A ) ORGANISM: CORYNEBACTERIUM SP ( x i ) SEQUENCE DESCRIPTION: SEQ ID NO:28:

GAGCGCACAC GCGGATGAGG TCG        23

( 2 ) INFORMATION FOR SEQ ID NO:29:

( i ) SEQUENCE CHARACTERISTICS:
        ( A ) LENGTH: 23 base pairs
        ( B ) TYPE: nucleic acid
        ( C ) STRANDEDNESS: single
        ( D ) TOPOLOGY: linear ( i i ) MOLECULE TYPE: DNA (genomic)

( i i i ) HYPOTHETICAL: NO ( i v ) ANTI-SENSE: NO ( v i ) ORIGINAL SOURCE:
        ( A ) ORGANISM: CORYNEBACTERIUM SP ( x i ) SEQUENCE DESCRIPTION: SEQ ID NO:29:

CGTGAGCGCA GCGCCCGATG AGG        23

( 2 ) INFORMATION FOR SEQ ID NO:30:

( i ) SEQUENCE CHARACTERISTICS:
        ( A ) LENGTH: 22 base pairs
        ( B ) TYPE: nucleic acid
        ( C ) STRANDEDNESS: single
        ( D ) TOPOLOGY: linear ( i i ) MOLECULE TYPE: DNA (genomic)

( i i i ) HYPOTHETICAL: NO ( i v ) ANTI-SENSE: NO ( v i ) ORIGINAL SOURCE:
        ( A ) ORGANISM: CORYNEBACTERIUM SP ( x i ) SEQUENCE DESCRIPTION: SEQ ID NO:30:

CGCGTGAGCG GGCACCCCGA TG        22

( 2 ) INFORMATION FOR SEQ ID NO:31:

( i ) SEQUENCE CHARACTERISTICS:
        ( A ) LENGTH: 23 base pairs
        ( B ) TYPE: nucleic acid
        ( C ) STRANDEDNESS: single
        ( D ) TOPOLOGY: linear ( i i ) MOLECULE TYPE: DNA (genomic)

( i i i ) HYPOTHETICAL: NO ( i v ) ANTI-SENSE: NO (v i) ORIGINAL SOURCE:
    (A) ORGANISM: CORYNEBACTERIUM SP (x i) SEQUENCE DESCRIPTION: SEQ ID NO:31:

GGGTCGCGTG GCGGCACACC CCG                     23

(2) INFORMATION FOR SEQ ID NO:32:

(i) SEQUENCE CHARACTERISTICS:
       (A) LENGTH: 22 base pairs
       (B) TYPE: nucleic acid
       (C) STRANDEDNESS: single
       (D) TOPOLOGY: linear (i i) MOLECULE TYPE: DNA (genomic)

(i i i) HYPOTHETICAL: NO (i v) ANTI-SENSE: NO (v i) ORIGINAL SOURCE:
       (A) ORGANISM: CORYNEBACTERIUM SP (x i) SEQUENCE DESCRIPTION: SEQ ID NO:32:

TCGGGTCGCG CGAGCGCACA CC                      22

(2) INFORMATION FOR SEQ ID NO:33:

(i) SEQUENCE CHARACTERISTICS:
       (A) LENGTH: 23 base pairs
       (B) TYPE: nucleic acid
       (C) STRANDEDNESS: single
       (D) TOPOLOGY: linear (i i) MOLECULE TYPE: DNA (genomic)

(i i i) HYPOTHETICAL: NO (i v) ANTI-SENSE: NO (v i) ORIGINAL SOURCE:
       (A) ORGANISM: CORYNEBACTERIUM SP (x i) SEQUENCE DESCRIPTION: SEQ ID NO:33:

CGGTTCGGGT GCGGTGAGCG CAC                     23

(2) INFORMATION FOR SEQ ID NO:34:

(i) SEQUENCE CHARACTERISTICS:
       (A) LENGTH: 23 base pairs
       (B) TYPE: nucleic acid
       (C) STRANDEDNESS: single
       (D) TOPOLOGY: linear (i i) MOLECULE TYPE: DNA (genomic)

(i i i) HYPOTHETICAL: NO (i v) ANTI-SENSE: NO (v i) ORIGINAL SOURCE:
       (A) ORGANISM: CORYNEBACTERIUM SP (x i) SEQUENCE DESCRIPTION: SEQ ID NO:34:

GGGCGACGGT GCCGGTCGCG TGA                     23

(2) INFORMATION FOR SEQ ID NO:35:

(i) SEQUENCE CHARACTERISTICS:
       (A) LENGTH: 22 base pairs
       (B) TYPE: nucleic acid

```
        ( C ) STRANDEDNESS: single
        ( D ) TOPOLOGY: linear ( i i ) MOLECULE TYPE: DNA (genomic)

( i i i ) HYPOTHETICAL: NO ( i v ) ANTI-SENSE: NO ( v i ) ORIGINAL SOURCE:
            ( A ) ORGANISM: CORYNEBACTERIUM SP ( x i ) SEQUENCE DESCRIPTION: SEQ ID NO:35:

GATCCGGGCG CGGGTTCGGG TC                                                    22
```

MUTANTS OF 2,5-DIKETO-D-GLUCONIC ACID (2,5-DKG) REDUCTASE A

CROSS REFERENCE TO RELATED APPLICATION

This application is a continuation-in-part of U.S. patent application Ser. No. 08/584,019, filed Jan. 11, 1996, now abandoned.

FIELD OF THE INVENTION

The present invention relates to improved mutant forms of an industrially valuable enzyme. More specifically, the invention relates to mutated forms of 2,5-diketo-D-gluconic acid (2,5-DKG) reductase A and B, naturally occurring variants of 2,5-DKG reductase. The mutated forms show improved catalytic activity for converting 2,5-DKG stereoselectively into 2-keto-L-gluconic acid (2-KLG), a precursor of ascorbic acid (vitamin C). The mutated forms may exhibit one or more of the following characteristics: improved temperature stability, increased resistance to substrate inhibition, increased turnover of the substrate by the enzyme and increased affinity for the substrate.

BACKGROUND OF THE INVENTION

Due to the expanding health consciousness of people around the world, there has been an increasing demand for vitamin C. Also contributing to the demand for ascorbic acid is its widespread use as an antioxidant for preserving food. One approach for satisfying this demand is to achieve increased production of 2-KLG, an intermediate in the production of ascorbic acid. The intermediate, 2-KLG, can be easily converted to ascorbic acid through acid or base catalyzed cyclization. It also has a greater stability and shelf life than ascorbic acid. Therefore, rather than producing ascorbic acid directly, it is more practical to stockpile 2-KLG for subsequent conversion to ascorbic acid.

A number of species of a first group of microorganisms, Erwinia, Acetobacter, and Gluconobacter, can produce 2,5-DKG from D-glucose. A second group of microorganisms from the coryneform group of bacteria (Corynebacterium, Brevibacterium, and Arthrobacter) as well as species of Micrococcus, Staphylococcus, Pseudomonas, Bacillus, and Citrobacter are capable of converting 2,5-DKG, produced by a microorganism of the first group, to 2-KLG. A tandem fermentation or cofermentation of appropriate microorganisms to produce 2-KLG was simplified by combining the relevant traits of both the Erwinia sp. and the Corynebacterium sp. in a single microorganism (Anderson et al., *Science* 23:144–149 (1985)). This was accomplished by identifying the 2,5-DKG reductase in the Corynebacterium sp. that converts 2,5-DKG into 2-KLG. The gene for this reductase was then cloned and expressed in *Erwinia herbicola*, a bacterium of the family Enterobacteriaceae that converts D-glucose into 2,5-DKG in a single fermentation. The resulting recombinant bacterial strain, with 2,5-DKG reductase as the pivotal enzyme, was able to convert D-glucose into 2-KLG in a single-fermentation process (Lazarus et al. *Fourth ASM Conf. Genet. Molec. Biol. Indust. Microorg.*, 187–193 (1989)).

Improving the catalytic efficiency of 2,5-DKG reductase, in the single-fermentation process, is a significant way to increase the production of 2-KLG. Also, a purified 2,5-DKG reductase A with increased catalytic activity could be used in an in vitro process for the conversion of 2,5-DKG to 2-KLG. For example, such a process would permit continuous production of 2-KLG through immobilization of the purified enzyme on a solid support.

According to the Michaelis-Menten scheme set out below, the

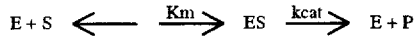

efficiency of an enzymatic reaction can be measured by two kinetic parameters, kcat and Km. The catalytic rate constant, kcat, also known as the turnover number, is a measure of the breakdown of the enzyme-substrate (ES) complex. It also represents the maximum number of substrate molecules (S) converted to product (P) via an ES complex per active site of the enzyme (E) per unit time. Vmax is the maximal velocity or rate of the enzyme catalyzed reaction when the enzyme is saturated with substrate. Therefore, Vmax is constant at saturating substrate concentration and remains unchanged with any increase in substrate concentration. The kcat at saturating substrate concentrations is related to Vmax and the total enzyme concentration, $[E_T]$, by the following equation: Vmax=kcat $[E_T]$. The Michaelis constant, Km, is the substrate concentration at which the velocity is equal to Vmax/2. Therefore, Km is a measure of the strength of the ES complex. In a comparison of Km's, a lower Km represents a complex with a stronger, more favorable binding, while a higher Km represents a complex with a weaker, less favorable binding. The ratio, kcat/Km, called the specificity constant, represents the specificity of an enzyme for a substrate, i.e., the catalytic efficiency per enzyme molecule for a substrate. The larger the specificity constant, the more preferred the substrate is by the enzyme.

Impressive yields of 2-KLG have been achieved with a Corynebacterium 2,5-DKG reductase (2,5-DKG reductase A, also known as 2,5-DKG reductase II) (Anderson et al., *Science* 230:144–149 (1985); Miller et al., *J. Biol. Chem.* 262:9016–9020 (1987)) expressed in appropriate host strains (2,5-DKG producers) such as Erwinia sp. These results have been achieved despite 2,5-DKG reductase A having a low reported specificity constant for 2,5-DKG.

This low reported specificity constant for 2,5-DKG reductase A is in contrast to a second, homologous Corynebacterium 2,5-DKG reductase (2,5-DKG reductase B, also known as 2,5-DKG reductase I) that has a reportedly greater specificity constant for 2,5-DKG (Sonoyama and Kobayashi, *J. Ferment. Technol.* 65:311–317 (1987)). In addition, both 2,5-DKG reductases are homologous to several known aldose and keto-reductases that have greater specificity constants towards their known substrates. Since Corynebacterium does not naturally encounter 2,5-DKG, it is not surprising that this compound is a poor substrate for 2,5-DKG reductase A. Such findings indicate that the active site of 2,5-DKG reductase A is not optimally configured for the catalytic conversion of 2,5-DKG to 2-KLG. Therefore, it appears that in order to optimize 2,5-DKG reductase A specific activity in the single-fermentation process, amino acid substitutions by site-directed mutagenesis must be made to the enzyme's active site.

In addition to improving an enzyme's kinetic parameters, site-directed mutagenesis can increase structural stability by amino acid substitutions, deletions, or insertions. The following are examples of structurally stabilizing mutations. The introduction of new disulfide bonds to create covalent crosslinks between different parts of a protein has been used to improve the thermal stability of bacteriophage T4 lysozyme (Matsumura et al., *Nature* 342:291–293 (1989)), bacteriophage λ repressor (Sauer et al., *Biochem.*

25:5992–5998 (1986)), *E. coli* dihydrofolate reductase (Villafranca et al., *Biochem.* 26:2182–2189 (1987)), and subtilisin BPN' (Pantoliano et al., *Biochem.* 26:2077–2082 (1987)). There is a computer program (Pabo et al., *Biochem.* 25:5987–5991 (1986)) that permits efficient scanning of the crystallographically determined three-dimensional structure of a protein to suggest those sites where insertion of two cysteines might lead to disulfide bonds. Such bonds would not disrupt the larger-scale conformation, while stabilizing the local conformation.

Amino acid substitutions of alanine for glycine in the α-helix have been shown to increase the thermal stability of the bacteriophage λ repressor (Hecht et al., *Proteins: Struct. Funct. Genet.* 1:43–46 (1986)) and the neutral protease from *Bacillus stearothermophilus* (Imanaka et al., *Nature* 324:695–697 (1986)). An increase in the melting temperature, $T_m$, for bacteriophage T4 lysozyme was accomplished by the two amino acid substitutions of proline for alanine and alanine for glycine (Matthews et al., *Proc. Nat. Acad. Sci. USA* 84:6663–6667 (1987)). Replacement of amino acids in the hydrophobic core of a protein with aromatic residues such as tyrosine, especially at positions near preexisting clusters of aromatic side chains, has been shown to promote thermal stability in kanamycin nucleotidyl transferase (Liao et al., *Biochem.* 83:576–580 (1986)) and bacteriophage λ repressor (Hecht et al., *Biochem.* 81:5685–5689 (1984)).

Transcriptional and translational control sequences in expression vectors are key elements required for the high level production of proteins in bacteria. The *E. coli* Trp, bacteriophage λP$_L$, *E. coli* lac UV5, and the Trp-lacUV5 fusion (Tac) promoters are among the most frequently used prokaryotic promoters (de Boer et al., *Proc. Nat. Acad. Sci. USA* 80:21–25 message, mRNA stability, and the protein's intrinsic stability are major factors in high-level expression.

Site-directed mutagenesis, using synthetic DNA oligonucleotides having the desired sequence, permits substitution, deletion, or insertion of selected nucleotides within a DNA sequence encoding a protein of interest. Recombinant DNA procedures are used to introduce the desired mutation by substituting the synthetic sequence for the target sequence. Development of plasmids containing an origin of replication derived from a filamentous bacteriophage (Vieira and Messing, *Methods in Enzymology* 153:3–11 (1987)) permits cloning of fragments into single stranded forms of plasmids capable of autonomous replication. Use of such plasmids eliminates the arduous task of subcloning DNA fragments from plasmids to filamentous bacteriophage vectors. Kits for carrying out site-directed mutagenesis are commercially available.

Mutants of 2,5-DKG reductase A having characteristics which vary from the native enzyme would be useful. In particular, one or more of the following characteristics: improved temperature stability, increased resistance to substrate inhibition, increased turnover of the substrate by the enzyme and increased affinity for the substrate would be useful to extend the commercial utility of the enzyme.

Unfortunately, unless proteins share regions of substantial sequence or structural homology, it is not possible to generalize among proteins to predict, based on a beneficial mutation of one protein, precisely where the sequence encoding another protein should be changed to improve the performance of that protein. Therefore, it is necessary to undertake an analysis of the precise structural and functional features of the particular protein to be altered. This suggests which amino acids to alter to produce a desired result, such as increased catalytic efficiency or thermal stability.

Increasingly, the correlation between the structures of known proteins and the sequence of a target protein is made using computer simulations (van Gunsteren, V. F., *Prot. Engin.* 2:5–13 (1988); Yang, M. M. et al., *In: Reaction Centers of Photosynthetic Bacteria*, (Michel-Beyerle, Ed.), Springer-Verlag, Germany (1990), pp 209–218), databases (Moult, J. et al., *Proteins* 1:146–163 (1987); Klein, P. et al., *Biopolymers* 25:1659–1672 (1986); Nakashima, H. et al., *J. Biochem.* 99:153–162 ((1986); Deleage, G. et al., *Prot. Engin.* 1:289–294 (1987)); neural networks (Qian, N. et al., *J. Molec. Biol.* 202:865–884 (1988); Holley, L. H. et al., *Proc. Natl. Acad. Sci. (U.S.A.)* 86:152–156 (1989); Bohr, H. et. al., *FEBS Lett.* 241:223–228 (1988)); or expert systems (Robson, B. et al., *J. Molec. Graphics* 5:8–17 (1987)). See, generally, Fasman, G. R., *TIBS* 14:295–299 (1989)).

The use of computers or computer-assisted methods in analyzing the structure of proteins is discussed, for example, in U.S. Pat. Nos. 4,704,692 (Ladner); 4,760,025 (Estell et al.); 4,853,871 (Pantoliano et al.); and 4,908,773 (Pantoliano et al.).

Sequence comparisons carried out using the sequence of 2,5-DKG reductase showed that it was a member of a larger superfamily of monomeric, NADPH-dependent prokaryotic and eucaryotic carbonyl reductases, known as the aldo-keto reductases (Carper et al., *Exp. Eye Res.* 49:377–388 (1989); Bohren et al., *J. Biol. Chem.* 264:9547–9551 (1989)). Members of this family of enzymes include: biosynthetic enzymes such as bovine prostaglandin F synthase; detoxifying enzymes such as chlordecone reductase and aflatoxin b1 reductase; and structural proteins with no identified enzymatic activity, such as rho crystallin from frog lens.

The human aldose reductase enzyme has been characterized and studied extensively. Aldose reductase has been implicated in diabetic complications; it is believed to cause reduction of glucose to sorbitol in diabetic patients, resulting in diabetic cataracts and the neuropathology associated with long-term diabetes. Significant efforts have been made to find specific aldose reductase inhibitors to prevent diabetic complications in humans (Frank, *Opthamology* 98:586–593 (1991); Zenon et al., *Clinical Pharmacy* 9:446–456 (1990). Due to its potential importance in human health, the crystal structure of human aldose reductase has been solved by several groups, either as the holoenzyme (Wilson et al., *Science* 257:81–84 (1992), in complex with NADPH cofactor or the cofactor analog ATP-ribose (Rondeau et al., *Nature* 355:469–472 (1992); Borhani et al., *J. Biol. Chem.* 267:24841–24847 (1992), or in complex with the inhibitor zopolrestat (Wilson et al., *Proc. Natl. Acad. Sci.* 90:9847–9851 (1993). Recently the structure of another aldo-keto reductase family member, alpha HSD, has also been solved (Hoog et al., *Proc. Natl. Acad. Sci.* 91:2517–2521 (1994). These structures show that the aldo-keto reductases are eight-fold alpha/beta parallel barrels also known as the 'TIM barrel' motif, after triose phosphate isomerase, where it was first described. This is an extremely common protein fold with ~17 examples known; about 10% of all enzymes whose structures are known are 'TIM barrels' (Farber and Petsko, *TIBS* 1990:228–235 (1990).

The structure of human aldose reductase reveals a number of features. The aldose reductase α/β barrel is composed of eight beta strands forming the barrel's 'core', surrounded by eight alpha helixes which are joined to the beta strands by loops of varying lengths. As in all known TIM-barrel enzymes, the loops found at the C-terminal ends of the beta strands comprise the enzymes' active site, where substrate and cofactor bind and catalysis occurs. NADPH is bound to the top of the barrel in an extended conformation, with the nicotinamide ring from which hydride transfer occurs occupying almost the exact center of the barrel. The orientation of the cofactor nicotinamide ring is as would be expected for an A-class reductase with the pro-R hydrogen protruding into the substrate binding pocket. There are two extra secondary structural features on the aldose reductase barrel: two additional alpha helices (denoted H1 and H2), which are found on the loops of amino acids joining beta strand seven and alpha helix seven, and in the C-terminal 'tail' after alpha helix eight. The structure of aldose reductase shows this C-terminal tail going over the top of the barrel to form part of the active site.

The present invention provides mutated forms of enzymatically active prokaryotic 2,5-DKG reductase A and 2,5-DKG reductase B.

SUMMARY OF THE INVENTION

The present invention provides mutants containing specific modifications of 2,5-DKG reductase A, 2,5-DKG reductase B and materials and methods useful in producing these proteins, as well as modified microorganisms and cell lines useful in their production. Other aspects of the invention include the expression constructs and products thereof for the modified 2,5-DKG reductases as well as cloning vectors containing the DNA encoding the modified 2,5-DKG reductases.

The DNA encoding the wild-type 2,5-DKG reductase A and the wild-type 2,5-DKG reductase B are modified using site-directed mutagenesis employing single stranded form of the genes that enable the generation of a change at a selected site within the coding region of either the 2,5-DKG reductase A or the 2,5-DKG reductase B. By this method, a change is introduced into isolated DNA encoding 2,5-DKG reductase A or 2,5-DKG reductase B which, upon expression of the DNA, results in substitution of at least one amino acid at a predetermined site in the 2,5-DKG reductase A or 2,5-DKG reductase B.

The modified 2,5-DKG reductases and coding sequences of the invention may exhibit one or more of the following characteristics: improved temperature stability, increased resistance to substrate inhibition, increased turnover of the substrate by the enzyme, and increased affinity for the substrate. The modified 2,5-DKG reductases may have varied Km and Vmax.

Another feature of the present invention, is that it provides a method for crystallization of 2,5-DKG reductase. A further feature of the present invention is that it provides a method for the crystallization of 2,5-DKG reductase complexed with NADPH.

BRIEF DESCRIPTION OF THE DRAWINGS

FIG. 3 shows plasmids ptrp1-35.A and prtp1-35.B.

FIG. 5 shows a comparison of the predicted secondary elements in 2,5-DKG Reductase A based on the algorithmic and homology model.

FIG. 6 show a protein sequence alignment of 2,5-DKG Reductase A and B with human aldose reductase. (SEQ ID NO:2) (SEQ ID NO:3) Boxes represent secondary structural elements in adolase reductase.

FIG. 11 shows the cofactor Km of 2,5-DKG Reductase A Mutants F22Y, Q192R, A272G, and F22Y/A272G compared with 2,5-DKG Reductases A and B.

FIG. 12 shows the thermal denaturation analysis of selected mutants compared with wild-type 2,5-DKG Reductases A and B.

DETAILED DESCRIPTION OF THE INVENTION

Definitions

Figure 1:
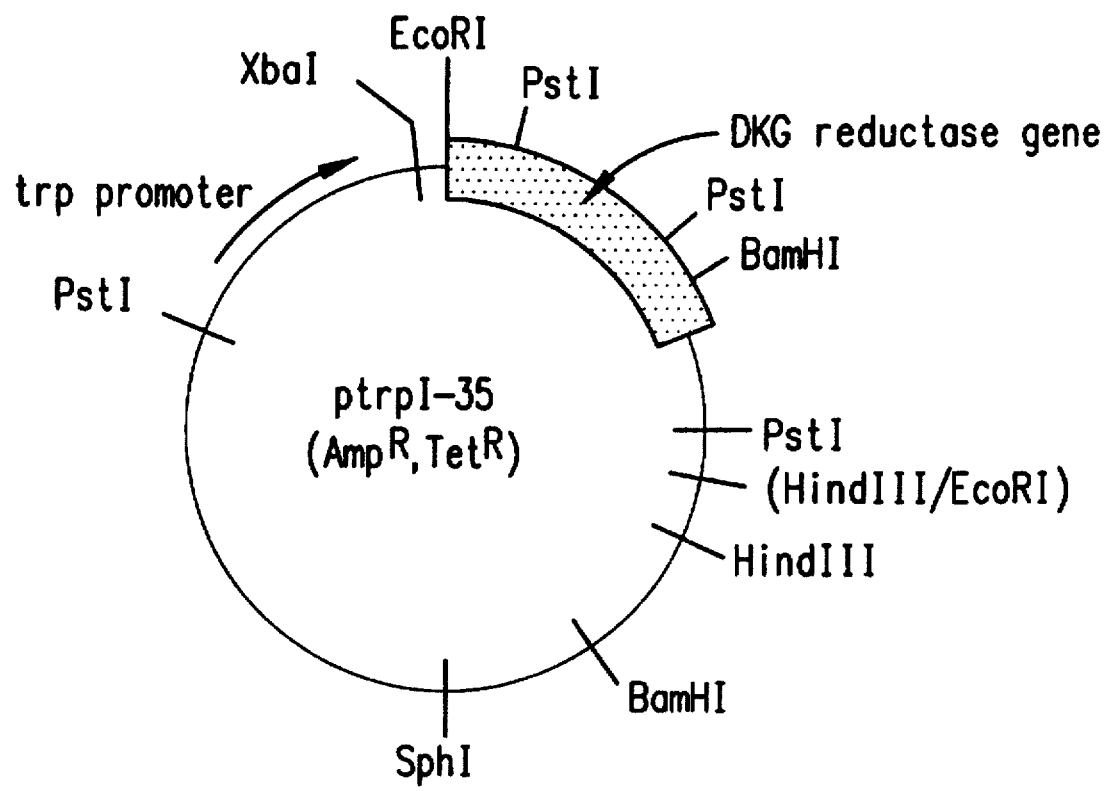
FIG. 1 shows an expression vector for the 2,5-DKG reductase A gene.

As used herein, the term "wild-type" 2,5-DKG reductase A refers to a protein which is capable of catalyzing the conversion of 2,5-DKG stereoselectively to 2-KLG. The wild-type enzyme is the enzyme obtained from the Corynebacterium sp. derived from ATCC strain No. 31090 as described in U.S. Pat. No. 5,008,193, incorporated herein by reference.

The term "wild-type" 2,5-DKG reductase B refers to a protein which is capable of catalyzing the conversion of 2,5-DKG stereoselectively to 2-KLG. The wild-type enzyme is the enzyme obtained from Corynebacterium sp. shs752001 as described by Hardy et al. U.S. Pat. No. 4,945,052, incorporated herein by reference.

As used herein, the term "mutant" in relation to a protein such as "wild-type" 2,5-DKG reductase A or "wild-type" 2,5-DKG reductase B, refers to a protein having a related amino acid sequence. However, it contains one or more amino acid substitutions, deletions, or insertions of amino acid residues. These residues have been selected by using certain approaches. One approach involves using secondary structural predictions to assign 2,5-DKG reductase A to an eight-stranded α/β barrel structure. A number of modifications can be undertaken to modify the gene to encode mutants of the enzyme with improved characteristics, compared to the wild-type enzyme, for converting 2,5-DKG stereoselectively into 2-KLG.

It is well understood in the art that many of the compounds discussed in the instant specification, such as proteins and the acidic derivatives of saccharides, may exist in a variety of ionization states depending upon their surrounding media, if in solution, or out of the solutions from which they are prepared if in solid form. The use of a term such as, for example, gluconic acid, to designate such molecules is intended to include all ionization states of the organic molecule referred to. Thus, for example, both "D-gluconic acid" and "D-gluconate" refer to the same organic moiety, and are not intended to specify particular ionization states. It is well known that D-gluconic acid can exist in unionized form, or may be available as, for example, the sodium, potassium, or other salt. The ionized or unionized form in which the compound is pertinent to the disclosure will either be apparent from the context to one skilled in the art or will be irrelevant. Thus, the 2,5-DKG reductase A protein itself and its various mutants may exist in a variety of ionization states depending on pH. All of these ionization states are encompassed by the terms "2,5-DKG reductase A" and "mutant form of 2,5-DKG reductase A."

The term "expression vector" includes vectors which are capable of expressing DNA sequences contained therein where such sequences are operably linked to other sequences capable of effecting their expression. It is implied, although not explicitly stated, that expression vectors must be replicable in the host organisms either as episomes or as an integral part of a chromosomal DNA. Clearly, a lack of replication would render them effectively inoperable. In sum, "expression vector" is also given a functional definition. Generally, expression vectors of utility in DNA recombinant techniques are often in the form of "plasmids". Plasmids refer to either circular double stranded DNA molecules or circular single stranded DNA molecules containing an origin of replication. These DNA molecules, in their vector form, are not linked to the chromosomes. Other effective vectors commonly used are phage and non-circular DNA. In the present specification, "plasmid" and "vector" are often used interchangeably. However, the invention is intended to include such other forms of expression vectors which serve equivalent functions and which are, or subsequently become, known.

The term "construct" is intended to broadly include plasmids, vectors, etc., and fragments thereof (such as cassettes, and gene sequences).

"Recombinant host cells", "host cell", "cells", "cell cultures" and so forth are used interchangeably to designate individual cells, cell lines, cell cultures, and harvested cells which have been or are intended to be transformed with the recombinant vectors of the invention. The terms also include the progeny of the cells originally receiving the vector.

"Transformation" refers to any process for altering the DNA content of the host. This includes in vitro transformation procedures such as calcium chloride, calcium phosphate or DEAE-dextran-mediated transfection, conjugation, electroporation, nuclear injection, phage infection, or such other means for effecting controlled DNA uptake as are known in the art.

The terms "amino acid" and "amino acids" refer to all naturally occurring L-α-amino acids. This definition is meant to include norleucine, ornithine, and homocysteine. The amino acids are identified by either the single-letter or three-letter designations:

| Asp | D | aspartic acid | Ile | I | isoleucine |
| Thr | T | threonine | Leu | L | leucine |
| Ser | S | serine | Tyr | Y | tyrosine |
| Glu | E | glutamic acid | Phe | F | phenylalanine |
| Pro | P | proline | His | H | histidine |
| Gly | G | glycine | Lys | K | lysine |
| Ala | A | alanine | Arg | R | arginine |
| Cys | C | cysteine | Trp | W | tryptophan |
| Val | V | valine | Gln | Q | glutamine |
| Met | M | methionine | Asn | N | asparagine |

These amino acids may be classified according to the chemical composition and properties of their side chains. They are broadly classified into two groups, charged and uncharged. Each of these groups is divided into subgroups to classify the amino acids more accurately:

I. Charged Amino Acids

Acidic Residues: aspartic acid, glutamic acid

Basic Residues: lysine, arginine, histidine

II. Uncharged Amino Acids

Hydrophilic Residues: serine, threonine, asparagine, glutamine

Aliphatic Residues: glycine, alanine, valine, leucine, isoleucine

Non-polar Residues: cysteine, methionine, proline

Aromatic Residues: phenylalanine, tyrosine, tryptophan

TABLE 1

| Original Residue | Conservative Substitutions |
| --- | --- |
| Ala | ser |
| Arg | lys |
| Asn | gln; his |
| Asp | glu |
| Cys | ser; ala |
| Gln | asn |
| Glu | asp |
| Gly | pro |
| His | asn; gln |
| Ile | leu; val |
| Leu | ile; val |
| Lys | arg; gln; glu |
| Met | leu; ile |
| Phe | met; leu; tyr |
| Ser | thr |
| Thr | ser |
| Trp | tyr |
| Tyr | trp; phe |
| Val | ile; leu |

Substantial changes in function or stabilization are made by selecting substitutions that are less conservative than those in Table 1, i.e., selecting residues that differ more significantly in their effect on maintaining (a) the structure of the polypeptide backbone in the area of the substitution, for example as a sheet or helical conformation, (b) the charge or hydrophobicity of the molecule at the target site or (c) the bulk of the side chain. The substitutions which in general are expected to produce the greatest changes will be those in which (a) a hydrophilic residue, e.g. serine or threonine, is substituted for (or by) a hydrophobic residue, e.g. leucine, isoleucine, phenylalanine, valine or alanine; (b) a cysteine or proline is substituted for (or by) any other residue; (c) a residue having an electropositive side chain, e.g., lysine, arginine, or histidine, is substituted for (or by) an electronegative residue, e.g., glutamic acid or aspartic acid; or (d) a residue having a bulky side chain, e.g., phenylalanine, is substituted for (or by) one not having a side chain, e.g., glycine.

General Methods

Most of the techniques which are used to transform cells, construct vectors, effect hybridization with a probe, carry out site-directed mutagenesis and the like, are widely practiced in the art. Most practitioners are familiar with the standard resource materials which describe specific conditions and procedures (see for example, Sambrook et al., *Molecular Cloning: A Laboratory Manual*, Cold Spring Harbor Press (1989), herein incorporated by reference. However, for additional guidance the following paragraphs are presented.

Expression of 2,5-DKG Reductase A

The complete functional gene is ligated into a suitable expression vector containing a promoter and ribosome binding site operable in the host cell into which the coding sequence will be transformed. In the current state of the art, there are a number of promotion/control systems and suitable prokaryotic hosts available which are appropriate to the present invention. Similar hosts can be used both for cloning and for expression since prokaryotes are, in general, preferred for cloning of DNA sequences. The method of 2-KLG production is most conveniently associated with such microbial systems. *E. coli* K12 strain 294 (ATCC No. 31446) is particularly useful as a cloning host. Other microbial strains which may be used include *E. coli* strains such as *E. coli* B, *E. coli* X1776 (ATCC No. 31537) and *E. coli* DH-1 (ATCC No. 33489). For expression, the aforementioned strains, as well as *E. coli* W3110 (F-, λ, prototrophic ATCC No. 27325), bacilli such as *Bacillus subtilus*, and other enterobacteriaceae such as *Salmonella typhimurium* or *Serratia marcesans*, and various Pseudomonas species may be used. A particularly preferred group of hosts includes those cultures which are capable of converting glucose or other commonly available metabolites to 2,5-DKG. Examples of such hosts are generally found among the genera Acetobacter, Gluconobacter, Acetomonas, and Erwinia. The taxonomy and nomenclature of these genera are such that the same or similar strains are sometimes given different names. For example, *Acetobacter cerinus* used in the example below is also referred to as *Gluconobacter cerinus*. Examples of particular hosts include but are not limited to, *Erwinia herbicola* ATCC No. 21998 (also considered an *Acetomonas albosesamae* in U.S. Pat. No. 3,998,697); *Acetobacter* (Gluconobacter) *oxydans* subspecies melanozenes, IFO 3292, 3293 ATCC No. 9937; *Acetobacter* (Gluconobacter) *cerinus* IFO 3263 IFO 3266; *Gluconobacter rubiginous*, IFO 3244; *Acetobacter fragum* ATCC No. 21409; *Acetobacter* (Acetomonas) *suboxydans* subspecies industrious ATCC No. 23776.

In general, plasmid expression or cloning vectors or conjugative plasmids containing replication and control sequences which are derived from species compatible with the host cell are used in connection with these hosts. The vector ordinarily carries a replication origin as well as marker genes which are capable of providing phenotypic selection in transformed cells. For example *E. coli* is typically transformed using pBR322, a plasmid derived from an *E. coli* strain (Bolivar et al., *Gene* 2:95-113 (1977)). pBR322 contains genes for ampicillin and tetracycline resistance and thus provides easy means for identifying transformed cells. For use in expression, the pBR322 plasmid, or other microbial plasmid must also contain, or be modified to contain, promoters which can be used by the microbial organism for expression of its own proteins. Those promoters most commonly used in recombinant DNA construction include the β-lactamase (penicillinase) and lactose promoter systems (Chang et al., *Nature* 273:615 (1978); Itakura et al., *Science* 198:1056-1063 (1977); Goeddel et al., *Nature* 281:544-548 (1979)) and a tryptophan (trp) promoter system (Goeddel et al., *Nucleic Acids Res.* 8:4057-4074 (1980); EPO Application No. 0036776). While these are the most commonly used, other microbial promoters have been discovered and utilized. Details concerning their nucleotide sequences have been published, enabling a skilled worker to ligate them functionally in operable relationship to genes in transformation vectors. (Siebenlist et al., *Cell* 20:269-281 (1980)).

By suitable cleavage and ligation, DNA sequences encoding 2,5-DKG reductase A and B can be included in the aforementioned vectors prepared as outlined above. Any unnecessary or inhibitory sequences may be deleted and the prokaryotic enzyme may then be purified; or the intact or broken cells used directly as catalysts. Alternatively, the host may be chosen so that once transformed it is capable of effecting the entire conversion of glucose or other suitable metabolite to the desired 2-KLG product.

Both the wild-type plasmid DNAs, the mutant plasmid DNA for 2,5-DKG reductase A and the mutant plasmid DNA for 2,5-DKG reductase B are transfected into a host for enzyme expression. The recombinant host cells are cultured under conditions favoring enzyme expression. Usually selection pressure is supplied by the presence of an antibiotic. The resistance to the antibiotic is encoded by the vector.

Vector Construction For Mutagenesis

Figure 2:
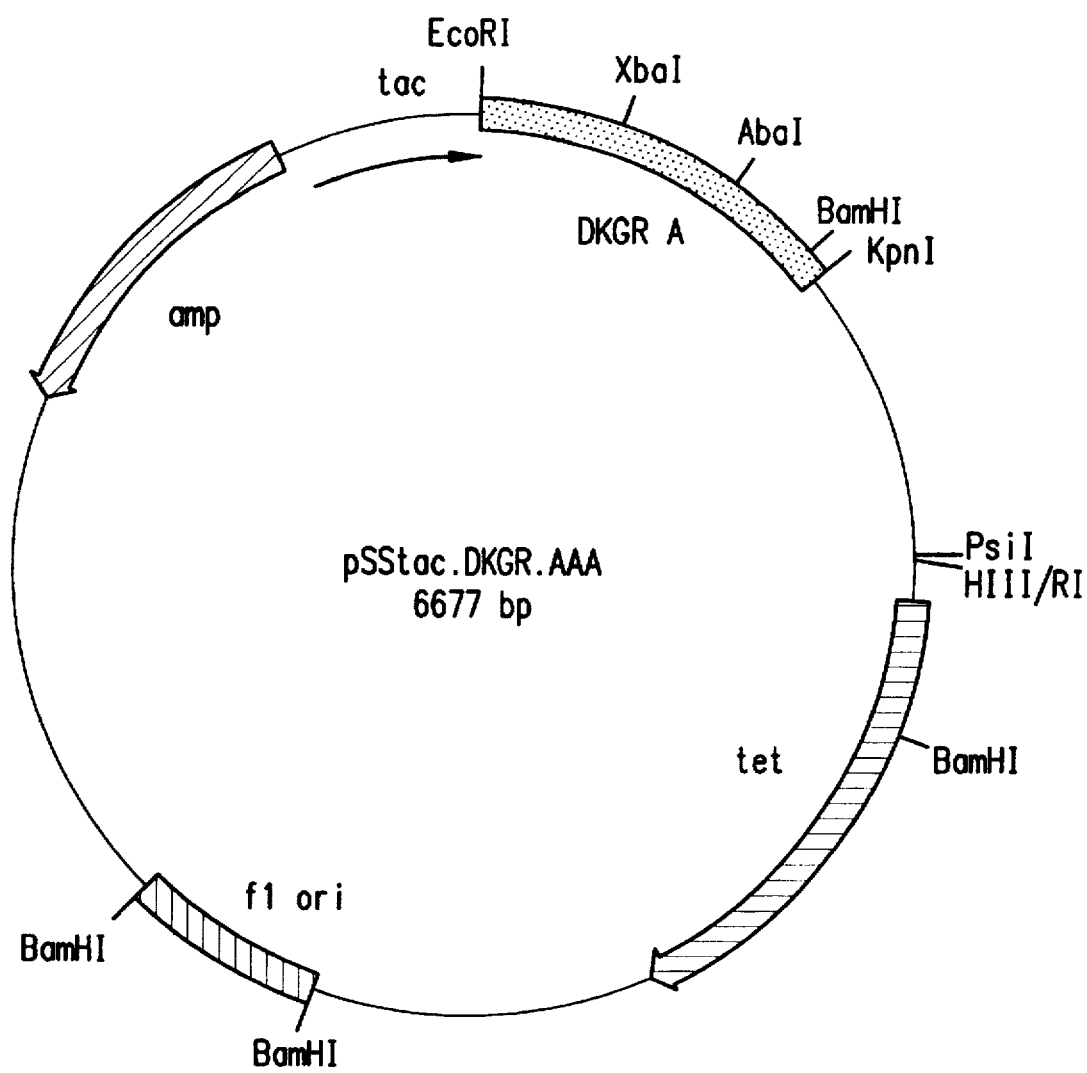
FIG. 2 shows an expression vector for producing mutant forms of 2,5-DKG reductase A.

Anderson et al. have described the construction of plasmid ptrp1-35 in U.S. Pat. No. 5,008,193, incorporated herein by reference, that contains the cloned DKG reductase A gene under the control of the *E. coli* trp promoter (FIG. 1). A derivative of this plasmid is constructed, with a few minor modifications to facilitate construction and characterization of mutant forms of 2,5-DKG reductase A. These modifications are described below. The final plasmid construct is called pSStac.DKGR.AAA and is shown in FIG. 2.

A) The structural gene for 2,5-DKG reductase A is mutated to include three new restriction enzyme sites to facilitate further mutagenesis studies. These three sites are "silent," i.e., the amino acid sequence of the resulting DKGR A protein remains unchanged.

B) The promoter in pSStac.DKGR.AAA is the tac II promoter described by de Boer et al (*Proc. Nat. Acad. Sci. USA* 80:21-25 (1983)) instead of the trp promoter found in ptrp1-35. This is a modified version of the trp promoter containing the binding site for lac repressor, allowing the expression of the gene to be regulated in cells expressing the lac repressor.

C) The plasmid is further modified to include the origin of replication from the single stranded filamentous phage f1. The use of this DNA sequence in plasmids is well known in the art to produce a single stranded form of the plasmid for sequencing and mutagenesis.

In order to produce 2,5-DKG reductases and mutants, two additional plasmids were constructed: ptrp1-35.A and ptrp1-35.B. (FIG. 3) which express the structural genes for 2,5-DKG reductase variants A and B, respectively, behind the *E. coli* trp promoter in a pBR322 derived vector. The starting point for these plasmid constructs was ptrp1-35 described in U.S. Pat. No. 5,008,193.

In preparing the genes for DKG reductase A and B for expression, a number of modifications to the wild-type coding sequences of these genes were made. The wild-type DKG reductase A gene plasmid in ptrp1-35 has a EcoRI site immediately upstream of the initiation methionine; a Kpn I site was introduced immediately after the termination codon to allow the entire structural gene to be excised in an EcoRI-KpnI digest. Similarly, EcoRI and KpnI sites were introduced immediately upstream and downstream of the wild-type DKG reductase B gene to allow the B gene to be placed into the same vector as the A gene.

The wild-type DKG reductase A gene was modified to introduce new XbaI and ApaI sites which, together with the flanking EcoRI and KpnI sites, subdivide the gene into three segments, each ~⅓ the length. The XbaI and ApaI sites in the A gene are 'silent', i.e. they do not alter the amino acid sequence of the encoded protein. The same two XbaI and ApaI sites were introduced into the analogous positions of the DKG reductase B gene. The first of the two sites, XbaI, is silent in the B gene and does not alter the amino acid sequence of the B gene. However it was not possible to introduce the second of the two sites (ApaI) into the B sequence without altering the amino acid sequence. A sequence variation was introduced therefore to accommodate the ApaI site: serine 189 of DKG reductase B was mutated to glycine (the amino acid found in the analogous position of the A gene) during creation of the ApaI site.

Plasmid ptrp1-35 was digested with EcoR1 and HindIII to generate a ~1690 b.p. fragment containing the structural gene for DKG reductase A and downstream sequence, which was purified by acrylamide gel electrophoresis and ligated into EcoR1 and HindIII digested M13mp19 vector DNA. Ligation reactions were transformed into *E. coli* strain JM101 cells; and the proper recombinants were identified by restriction mapping of recombinant phage RF preparations. The recombinant phage (M19mp19. EcoR1/HindIII.DKGRA) was prepared as a large scale template preparation (single stranded form) for mutagenesis reactions.

The starting point for plasmids containing the wild-type DKGR B gene is the plasmid pCBR13 as described (Grindley et al., *Applied and Environmental Microbiology* 54:1770–1775 (1988)) incorporated herein by reference. Plasmid pCBR13 was digested with EcoR1 and BamH1 to generate a ~2000 bp fragment, which was purified by acrylamide gel electrophoresis, and ligated into EcoR1 and BamH1 digested M13mp19 to generate recombinant phage M13mp19.R1/BamH1.DKGRB. The recombinant phage (M13mp19.R1/BamH1.DKGRB) was prepared as a large scale template preparation (single stranded form) for mutagenesis reactions.

Mutagenesis reactions were as follows. Oligonucleotide primers were designed to introduce new restriction sites into the wild-type DKGR A and B genes: for DKGR A: XbaI, ApaI, and KpnI were introduced; for DKGR B: EcoRI, ApaI, XbaI, and KpnI sites were introduced. (The oligonucleotide used to introduce these restriction sites were as follows:

XbaI.A=5'-C GCG AAG CTG GCT CTA GAT CAG GTC GAC-3'(SEQ ID NO:4),

ApaI.A=5'-A TCG TGG GGG CCC CTC GGT CAG GGC-3'(SEQ ID NO:5),

KpnI.A=5'-GAG GTC GAC TGA GGT ACC CGA ACA CCC G-3'(SEQ ID NO:6),

EcoRI.B=5'-GGG TAT CTA GAA TTC TAT GCC GAA-3' (SEQ ID NO:7),

XbaI.B=5'-C GAC CGG CTG GGT CTA GAC GTG ATC GAC -3'(SEQ ID NO:8),

ApaI.B=5'-ACC GAG AGC TGG GGG CCC CTC GCC CGG CGC-3'(SEQ ID NO:9),

KpnI.B=5'-GAA GAG ATG TAG GGT ACC GAT GCC GCG CAC-3'(SEQ ID NO:10).

Mutagenesis reactions were by the 'two-primer' method as described by Carter, *Methods Enzymol.* 154:382. (1987), herein incorporated by reference. Mutagenic oligonucleotides were diluted to 10 $OD_{260}$ units per ml. A kinase reaction was carried out as follows: 2 μl primer, 2 μl of 10×kinase buffer, 1 μl of 100 mM DTT, 13.5 μl of double-distilled and deionized $H_2O$, and 0.5 μl kinase (4 units/μl, New England Biolabs, Beverly, Mass.) for 30 minutes at 37° C. The kinase was then heat inactivated by incubation at 70° C. for 15 minutes and the reaction adjusted to 5 μM primer concentration. Annealing reactions were set up containing 5 μl of each appropriate primer at 5 μM, 5 μl of a similarly kinased and 'upstream' primer, (a sequencing 18-mer which is complementary to sequence immediately upstream of the M13 polylinker cloning site (5'-TTC CCA GTC ACG ACG TTG-3'), 3 μg of template, 2.5 μl of 10×RB buffer in a final volume of 25 μl and annealed by heating to 75 degrees centigrade in a heating block for 3 minutes, then allowed to cool to 25° C. on the benchtop.

Extensions were done by addition of 2 μl of 2.0 mM dATP, dCTP, dGTP, and dTTP; plus 1 μl ligase (6 Weiss units/μl, New England Biolabs, Beverly, Mass.), 1 μl Klenow fragment of *E. coli* DNA polymerase (5 units/μl, large fragment of DNA polymerase I, New England Biolabs, Beverly, Mass., 5 μl of 5×ligase buffer, 2 μl of 10 mM rATP, and $H_2O$ to a total of 50 μl. Extension was done at 25° C. for 4 hours. Five μl of the extension reaction was transformed into $CaCl_2$ competent MutL *E. coli* cells. Individual plaques were arrayed in a 96 well microtiter plate, grown at 37° C., stamped onto a lawn of *E. coli* strain JM101 cells and grown again at 37° C. Multiple nitrocellulose filter lifts were made of each plate and probed with the $^{32}P$ radiolabelled mutagenic oligonucleotides. Conditions were as follows: hybridization for one hour at 37° C., washed with 6×SSC at 37° C., then with TMACl wash solution (3M tetramethylammonium chloride, 50 mM Tris pH 8.0, 2 mM EDTA, and 0.1% SDS at 65 and 68° C. Individual putative recombinants that hybridized with all of the appropriate oligonucleotides were prepared in a single stranded form and sequenced to confirm that all the correct sites were present and that no secondary mutations had been introduced. The mutant phage thus identified were named:

'M13mp19.RI/HindIII.*DKGR*.AAA' and

'M13mp19.RI/BamHI.*DKGR*.BBB'.

The mutated genes were subcloned from phage back into ptrp1-35 vector for expression. Template of M13mp19.RI/HindIII.DKGR.AAA was 'filled in' with *E. coli* DNA polymerase Klenow fragment (5 units/μl, large fragment of DNA polymerase I, New England Biolabs, Beverly, Mass.) using all four dNTP's to generate a double stranded form in the following reaction: 25 μl template, 5 μl of 10×nick-translation buffer, 3 μl of 10 mM dATP, dCTP, dGTP, dTTP, 10 μl of M13-complementary 'upstream' primer (5'-TTC CCA GTC ACG ACG TTG-3'(SEQ ID NO:11)), in a total volume of 52 μl. Reactions were slow-annealed in a heating block as before, and initiated by addition of 1 μl of *E. coli* DNA polymerase Klenow fragment (5 units/μl, large fragment of DNA polymerase I, New England Biolabs, Beverly, Mass.), and extended for 30 minutes at 25° C. The reaction mixture was then digested with EcoRI and HindIII and the resulting 1690 bp fragment was purified and subcloned into ptrp1-35 digested with EcoRI and HindIII to generate plasmid ptrp1-35.DKGR.A. For the DKGR B construct, template M13mp19. EcoRI/BamHI.DKGR.BBB was similarly filled in, digested with EcoRI and KpnI, and this ~843 bp fragment purified by acrylamide gel electrophoresis. This fragment was then cloned into EcoRI/KpnI digested ptrp1-35.A (replacing the mutagenized DKGR A gene, but retaining the DKGR A downstream sequences from KpnI to Hind III). This plasmid is called ptrp1-35.DKGR.B:S189G.

The DKGR B expressing construct ptrp1-35.DKGR.B:S189G was used as a starting point to construct a wild-type DKGR B expressing plasmid, with the proper codon for serine at position 189. This was done as follows: ptrp1-35.B:S189G was digested with NcoI and XhoI to remove the internal ~⅔ (~700 bp) of the coding sequence, this region includes the introduced XbaI and ApaI sites as well as the serine to glycine mutation at amino acid 189. This region was replaced with the wild-type gene sequence from NcoI to XhoI from pCBR13. The final construct is called ptrp1-35.DKGR.B.

In order to produce protein of 2,5-DKG reductase A and B for characterization, the plasmids ptrp1-35.A and ptrp1-35.B, along with pBR322 control plasmid were introduced into *E. coli* strain HB101 by a $CaCl_2$ method and selected on LB agar plates containing ampicillin and tetracycline. 5.0 ml cultures were grown to saturation overnight in LB plus ampicilllin plus tetracycline at 37° C. with shaking. Cells were recovered by centrifugation and aliquots were analyzed by SDS-PAGE gel electrophoresis. No new bands were seen in the ~30,000 mw range expected for 2,5-DKG reductase in these cell lysates, nor in similar experiments with *E. coli* strain MM294. Cell lysates were assayed for 2,5-DKG reductase activity, and no activity was seen in these lysates over the pBR322 lysate background.

When these plasmids were similarly introduced into *Acetobacter cerinus* strain (IFO 3263) grown at the 28° C., and checked for expression by SDS-PAGE electrophoresis, prominent new bands in the ~30,000 dalton range were seen in the ptrp1-35.A and ptrp1-35.B lysates. Assays of the *Acetobacter cerinus* cell lysates for 2,5-DKG reducing activity also showed increased activity above pBR322 background.

Site-Directed Mutagenesis

The DNA sequence encoding the 2,5-DKG reductase A or 2,5-DKG Reductase B is subjected to site-directed mutagenesis to substitute nucleotides encoding selected amino acids at the predetermined positions within the sequence.

The preferred procedure for site-directed mutagenesis, where only a single base pair is to be altered, is performed by cloning the DNA sequence encoding the wild-type enzyme into a recombinant plasmid containing an origin of replication derived from a single-stranded bacteriophage. Then an appropriate primer is used to convert a nucleotide at an identified position. A synthetic oligonucleotide primer complementary to the desired sequence, except in areas of limited mismatching, is used as a primer in the synthesis of a strand complementary to the single-stranded wild-type 2,5-DKG reductase A or 2,5-DKG reductase B sequence in the plasmid vector. The resulting double-stranded DNA is transformed into a host bacterium. Cultures of the transformed bacteria are plated on agar plates, permitting colony formation from single cells which harbor the plasmid. Theoretically, 50% of the colonies will consist of plasmid containing the mutant form; 50% will have the original sequence. The colonies are hybridized with radiolabelled synthetic primer under stringency conditions which permit hybridization only with the mutant plasmid which will form a perfect match with the probe. Hybridizing colonies are then picked and cultured, and the mutant plasmid DNA is recovered.

Subsequent site directed mutagenesis may be used to alter additional nucleotides in any mutant. Alternatively, mutants with more than one altered nucleotide can be constructed using techniques that practitioners are familiar with such as isolating restriction fragments and ligating such fragments into an expression vector. (see for example, Sambrook et al., *Molecular Cloning: A Laboratory Manual*, Cold Spring Harbor Press (1989).

Selection Of Sites For Mutagenesis Of Mutants For The Wild-Type 2,5-DKG Reductase A Gene Crucial to selection of sites for mutagenesis is prediction of a secondary and tertiary structure of the wild-type enzyme. The secondary structural predictions are carried out in one of the following ways. First, the sequences of 2,5 DKG reductases A and B, and five other homologous enzymes ( prostaglandin F synthase, bovine reductase, h lens aldose reductase, human liver aldehyde reductase, and p-crystallin from frog eye lens) are aligned to reveal a number of conserved residues. Second, the sequences are subjected to a number of structure prediction algorithms (Chou and Fasman, *Adv. Enzymol.* 47:45–148 (1978); Gar- nier et al., *J. Mol. Biol.* 120:97–120 (1978); Wilmot and Thornton, *J. Mol. Biol.* 203:221–232 (1988); Karplus and Schulz, *Naturwissenschaften* 72:212–214 (1985); Eisenberg et al., *Proc. Nat. Acad. Sci. USA* 81:140–144 (1984); Rose and Roy, *Proc. Nat. Acad. Sci. USA* 77:4643–4647 (1980)) well known in the art. These predictions are collated and compared to derive a rough model of the enzyme's secondary structure as an eight-stranded ($\alpha/\beta$ barrel ("algorithmic model"). This secondary structure prediction is consistent with the recently solved secondary structures of homologous enzymes having the fold of an eight-stranded $\alpha/\beta$ barrel (Rondeau et al., *Nature* 355:469–472 (1992); Wilson et al., *Science* 257:81–84 (1992)).

The barrel structure is composed of two components. The first component is a core of eight twisted parallel beta strands arranged close together, like staves, into a barrel. Surrounding this barrel structure is a second component of eight alpha helices that are joined to the beta strands through loops of various lengths. This eight-stranded $\alpha/\beta$ barrel structure is called the triosephosphate isomerase (TIM) barrel from the enzyme for which this structure was first observed. The folding pattern of the $\alpha/\beta$ barrel is found in 17 enzymes whose crystal structures are known. In fact, approximately 10% of known enzyme structures are $\alpha/\beta$ barrels (Farber and Petsko, *TIBS* 15:228–234 (1990)). The 17 known $\alpha/\beta$ barrel enzymes have a common $\alpha/\beta$ barrel core; substrate and cofactor specificity comes from the variable loops joining the beta strands and alpha helices.

Figure 4:
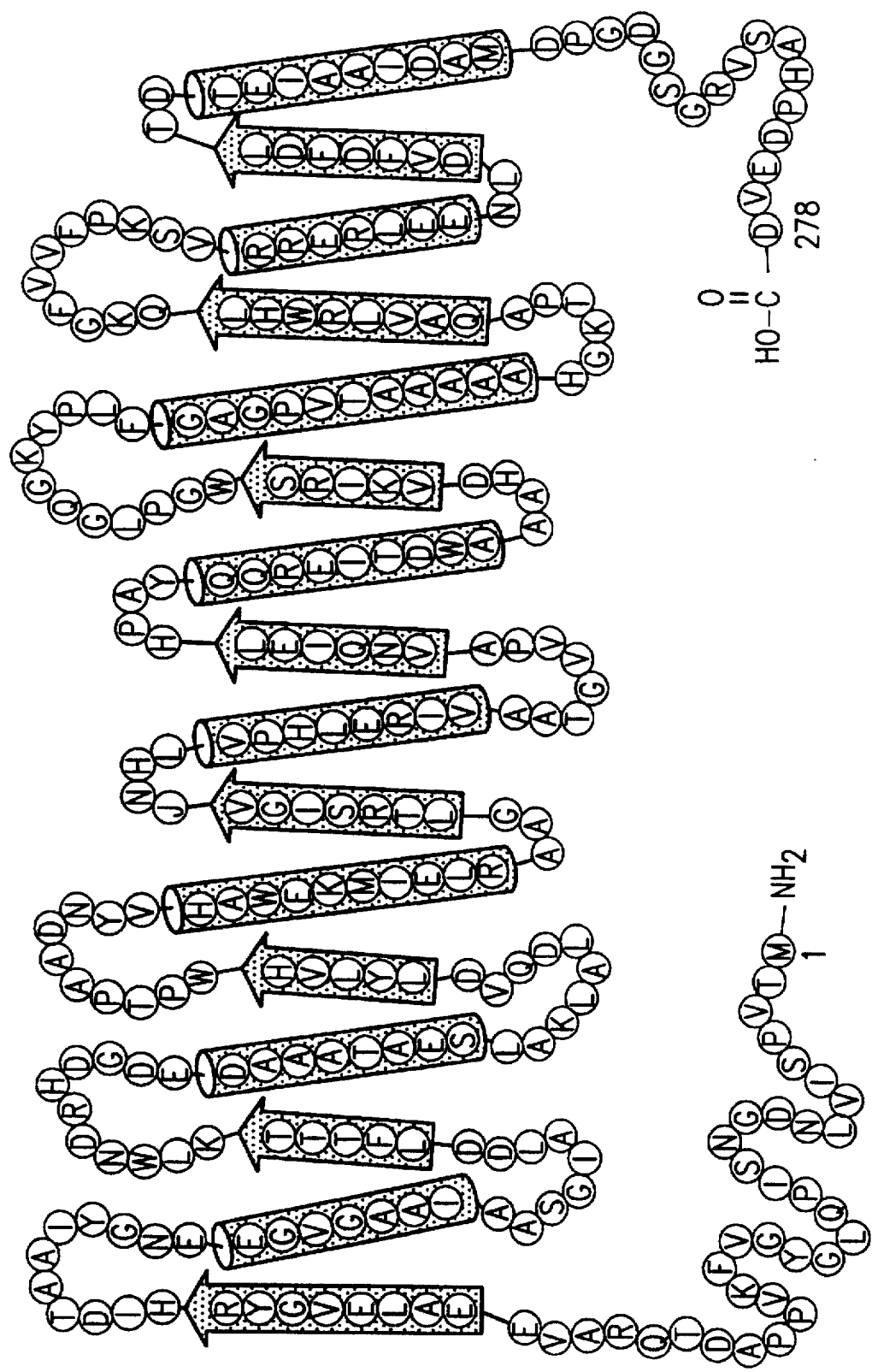
FIG. 4 shows schematically an algorithmic model for 2,5-DKG reductase A. (SEQ ID NO:1)

A proposed secondary structure model for 2,5-DKG reductase A, based on the algorthmic model (see above), is shown schematically in FIG. 4, where beta strands are represented by arrows and the alpha helices are shown as cylinders. Regions of polypeptide chain connecting the predicted elements of secondary structure are indicated as of undefined structure. There are N and C terminal extensions of 34 and 17 amino acids, respectively. Some subset of the eight loops at the C terminus of the beta sheet (towards the left of FIG. 4 (SEQ ID NO:1)), as well as the C-terminal "tail" (positions 262 to 278) are thought to comprise the active site of the enzyme, as in the other TIM-barrel enzymes. Although only a rough model, this structure greatly facilitates rational engineering of the enzyme, by allowing the focus towards those residues found in proposed active site loops. It is apparent that additional residues near to those in the proposed loops and "tail" may also comprise part of the active site.

Selection of sites for mutagenesis is enhanced by further comparative structural analysis. Sequence analysis of 2,5-DKG reductase revealed it to be a member of a larger superfamily of monomeric, NADPH-dependent prokaryotic and eucaryotic carbonyl reductases, known as the aldo-keto reductases (Carper et al., *Exp. Eye Res.* 49:377–388 (1985); Bohren, et al., *J. Biol Chem.* 264:9547–9551 (1989). Members of this group include biosynthetic enzymes such as bovine prostaglandin F synthase, detoxifying enzymes such as chlordecone reductase and aflatoxin b1 reductase, as well as structural proteins with no identified enzymatic activity, such as rho crystallin from frog lens.

The structure of human aldose reductase reveals a number of key features of significance in the homology modeling. The aldose reductase $\alpha/\beta$ barrel is composed of eight beta strands forming the barrel's 'core', surrounded by eight alpha helixes which are joined to the beta strands by loops of varying lengths. As in other known TIM-barrel enzymes, the loops found at the C-terminal ends of the beta strands comprise the enzymes' active site, where substrate and cofactor bind and catalysis occurs. NADPH is bound to the top of the barrel in an extended conformation, with the nicotinamide ring from which hydride transfer occurs occupying almost the exact center of the barrel. The orientation of the cofactor nicotinamide ring is as would be expected for an A-class reductase with the pro-R hydrogen protruding into the substrate binding pocket. There are two extra secondary structural features on the aldose reductase barrel: two additional alpha helices (denoted H1 and H2), which are found on the loops of amino acids joining beta strand seven and alpha helix seven, and in the C-terminal 'tail' after alpha helix eight. The structure of aldose reductase shows this C-terminal tail going over the top of the barrel to form part of the active site.

A model of 2,5-DKG reductase variant A was built based on the coordinates of the aldose reductase:NADPH complex (Wilson et al., Science 257:81–84 (1992)), applying modeling methods (Greer, Methods in Enzymology 202:239–252 (1991); Bajorath et al., Protein Science 2:1798–1810 (1993); both herein incorporated by reference). FIG. 5 shows the secondary elements predicted by this model.

Such information as to which amino acids comprise the active site of an enzyme can be gained from knowledge of the actual three dimensional shape of the enzyme in question, as obtained from x-ray crystallographic or NMR studies. In the case of 2,5-DKG reductase, no such equivalent information yet exists in the published literature. Therefore, an alternate strategy in such a case would be using the models for 2,5-DKG reductase A, as discussed above, to limit the possible single amino acid replacements, or combinations of single amino acid replacements, to those residues found associated with active site areas.

Mutations at particular sites in a protein can lead to enhanced expression of that protein in bacteria. Many of the other possible point mutants are generated in clusters of one to four closely spaced amino acid substitutions. Of the mutants which are stably folded, only those falling in the 21–25 region, 46–52 region, 164–170 loop, 188–200 loop, 230–235 loop, and C-terminal "tail" (262–278) exhibit activity significantly different from the wild type enzyme. This is additional confirmation that these loop and tail regions comprise the enzyme active site.

Any number of mutations proposed herein may be combined in a single mutant. Obviously, a particular substitution at one location rules out replacement with another amino acid at that same location in that particular mutant.

The following examples are presented to illustrate the present invention and to assist one of ordinary skill in making and using the same. The examples are not intended in any way to otherwise limit the scope of the invention.

EXAMPLE 1

Construction Of Plasmid pSStac.DKGR.AAA For Mutagenesis

An aliquot of plasmid ptrp1-35 was digested with EcoRI and HindIII restriction enzymes and the resulting 1690 base pair fragment purified by agarose gel electrophoresis. This fragment was then ligated into EcoRI and HindIII digested vector M13 mp19. The resulting recombinant phage (called M13 mp19.DKGRA) was used to isolate a single stranded template form of the phage for subsequent mutagenesis. The template was mutagenized with three oligonucleotides to introduce three new restriction enzyme cleavage sites to the 2,5-DKG reductase A gene. These sites are all 'silent' in that although they introduce a new restriction cleavage site to the DNA sequence, the amino acid sequence of the protein coded for remains unchanged, due to degeneracy in the genetic code. The three mutagenic oligonucleotides and the changes introduced are as follows: 1) oligonucleotide XbaA has sequence 5'CGCGAAGCTGGCTCTAGATCAGGTC-GAC 3'(SEQ ID NO:12) and introduces a new XbaI site at amino acid position 98; 2) oligonucleotide ApaA has sequence 5'ATCGTGGGGGCCCCTCGGTCAGGGC 3'(SEQ ID NO:13) and introduces a new ApaI site at amino acid position 188; and 3) oligonucleotide KpnA has sequence 5'GAGGTCGACTGAGGTACCCGAACACCCG 3'(SEQ ID NO:14) and introduces a new KpnI site immediately following the stop codon (TGA) after the final amino acid. The mutagenesis reaction and conditions were essentially the same as described in Example 2 for the construction of mutant Q192R. After the mutagenesis reaction, positive plaques were identified by hybridization to the mutagenic oligonucleotide under stringent conditions, and the entire coding region of the 2,5-DKG reductase A fragment was sequenced to confirm the mutations.

The plasmid pSStac.DKGR.AAA was constructed as a three way ligation of the following fragments: 1) EcoRI to HindIII from the mutagenized phage M13 mp19.DKGRA as described above, this contains the coding gene for 2,5-DKG reductase A; 2) the PstI to EcoRI fragment (850 base pairs) from plasmid ptac6 (ptac6 is equivalent to plasmid ptrp1-35 but contains the tac promoter as described in de Boer et al. (Proc. Nat. Acad. Sci. USA 80:21–25 (1983)) instead of the trp promoter found in ptrp1-35), and 3) the ~4,000 base pair vector fragment from HindIII to PstI of plasmid p690. The p690 plasmid is a derivative of plasmid pBR322 with the RsaI/DraI restriction fragment from the genome of bacteriophage f1 (nucleotides 5489–5946), containing the single-stranded DNA origin of replication, inserted into the PvuII site.

The three fragments described above were isolated by agarose gel electrophoresis, purified, and ligated in approximately equimolar ratios, and used to transform competent E. coli cells. The resulting colonies were analyzed by restriction mapping to identify the correct construct, called pSStac.DKGR.AAA (FIG. 2).

EXAMPLE 2

Site-Directed Mutagenesis Of The 2,5-DKG Reductase A Gene

A. Preparation of Template DNA For Mutagenesis E. coli cells (strain XL1-Blue, Stratagene Corporation) bearing plasmid pSStac.DKGR.AAA were grown in LB media (Sambrook et al., Molecular Cloning: A Laboratory Manual, Cold Spring Harbor Press, A.1 (1989)) to early log phase, and infected with helper phage VCS-M13 (Stratagene). Infection with helper phage provides needed factors for the packing and secretion of the single-stranded form of plasmid pSStac.DKGR.AAA. The infected cells were grown overnight with shaking at 37° C., and the next day the cells were removed by centrifugation at 10,000 rpm for 10 minutes in a Sorvall SM24 rotor. The supernatant containing the packaged plasmid was retained and the cell pellet discarded. The packaged plasmid was precipitated by the addition of ¼ volume of 2.5M NaCl, 20% PEG (polyethylene glycol). After addition the mixture was stored at 25° C. for 20 minutes, and then the precipitate was recovered by centrifugation.

The precipitate was dissolved in 0.4 ml of TE buffer (10 mM tris, pH 7.5, 1 mM EDTA) and further purified by several sequential extractions with an equal volume of 50:50 chloroform:phenol. After each extraction the aqueous (upper) phase was retained. The DNA was precipitated with 2 volumes of ice-cold ethanol. The precipitate was recovered by centrifugation and dissolved in TE buffer. The concentration of the plasmid was estimated by measuring the optical absorbance at 260 nm using the conversion of 1 $OD_{260}$=40 µg of single stranded DNA per milliliter. The concentration of the plasmid was adjusted to 1 µg per ml with TE.

B. Phosphorylation Of Oligonucleotide Primer

A synthetic oligonucleotide with the sequence 5'GCCCCTCGGTCGCGGCAAGTACG 3'(SEQ ID NO:15) was synthesized and phosphorylated as follows: the oligonucleotide was diluted to a concentration of 5.0 $OD_{260}$ units per ml. Then 2.5 µl of oligonucleotide was combined with 3 µl 10×kinase buffer (1M tris pH 8.0, 100 mM $MgCl_2$, 70 mM dithiothreitol, 10 mM ATP), 25 µl water, and 2 units of T4 polynucleotide kinase (4 units/µl, New England Biolabs, Beverly, Mass.). The mixture was incubated at 37° C. for 15 minutes, then the kinase enzyme was inactivated by heating to 70° C. for 10 minutes.

C. Mutagenesis Reaction

Six µl of kinased primer were combined with 1 µg of template DNA and 2.5 µl of 10×RB buffer (70 mM tris, pH 7.5, 50 mM mercaptoethanol, 550 mM NaCl, and 1 mM EDTA) in a total volume of 10.5 µl. The primer was annealed to the template by heating the mixture to 65° C. for five minutes, then slowly cooling to 25° C. over a 30 minute period.

To the annealing mixture was added 1.5 µl of 10×RB buffer, 1 µl of 10 mM ATP, 1 µl of 10 mM DTT (dithiothreitol), and 1 µl T4 DNA ligase (6 Weiss units/µl, New England Biolabs, Beverly, Mass.). After 10 minutes, 1 µl of 1M $MgCl_2$, 1 µl of 5 mM dNTP's (an equimolar mixture of dATP, dCTP, dGTP, and dTTP) and 0.5 µl of Klenow (5 units/µl, large fragment of DNA polymerase I, New England Biolabs, Beverly, Mass.) were added, and the mixture incubated at 15° C. overnight.

The following day, frozen competent *E. coli* MutL cells were transformed with an aliquot of the reaction mixture, and plated onto agar plates containing antibiotic selection (12.5 µg/ml tetracycline, 50 µg/ml ampicillin). Colonies bearing mutant plasmids were initially identified by hybridization to the original mutagenic oligonucleotide under stringent conditions (Wood et al, *Proc. Nat. Acad. Sci. USA* 82:1585–1588 (1988)). Mutant plasmids were then prepared in a single-stranded form as in Section A and confirmed by direct DNA sequencing of the plasmid (United States Biochemical Corporation, Sequenase sequencing kit). The resulting mutant Q192R 2,5-DKG reductase A, as shown in Example 5, had improved catalytic activity in comparison to the wild-type 2,5-DKG reductase A.

EXAMPLE 3

Expression Of Wild-Type 2,5-DKG Reductase A In Acetobacter Cerinus

Plasmid DNA was introduced into *Acetobacter cerinus* (ATCC No. 39140) by electroporation, as described (Wirth et al, *Mol. Gen. Genet.* 216(1):175–177 (1989)) using a Genepulser apparatus (Biorad Corporation). Cells were grown to mid-log phase ($OD_{550}$ ~0.2–0.8) in 100 ml LB medium and recovered by centrifugation at 5,000 rpm in a Sorvall SS-34 rotor for 5 minutes at 4° C. The cells were resuspended in one half volume of ice-cold electroporation buffer (300 mM sucrose, 7 mM sodium phosphate buffer, pH 7.0, and 1 mM $MgCl_2$), again pelleted by centrifugation, and finally resuspended in 1/20th volume of electroporation buffer, and stored on ice until use.

Plasmid DNA (0.1 to 1.0 µg) was added to a 0.4 cm electroporation cuvette (Biorad Corporation) which contained 0.8 ml of the prepared Acetobacter cells. The cells and DNA were mixed in the cuvette and cooled on ice for 10 minutes prior to electroporation. The cells and DNA were given a single pulse at 2500 mV using a 25 uF capacitor setting, and immediately diluted to 3.0 ml with fresh LB media. The diluted cells were then allowed to recover with shaking at 30° C. for 2 hours. Aliquots (10–100 µl) of the transformed cells were plated on selective media (LB agar plates containing 50 µg/ml ampicillin and 12.5 µg/ml tetracycline) and the plates were grown overnight at 30° C.

EXAMPLE 4

Purification Of The Mutant Q192R And The Wild-Type 2,5-DKG Reductase A

Single colonies from transformed *Acetobacter cerinus* cells were grown in 200 mls of 2×YT media (Sambrook et al., *Molecular cloning: A Laboratory Manual*, Cold Spring Harbor Press, A.3 (1989)) containing antibiotics (12.5 µg/ml tetracycline and 50 µg/ml ampicillin) at 30° C. overnight. The cells were recovered by centrifugation (15 minutes at 8000 rpm in a Sorvall GS3 rotor) and stored frozen. The cells were then thawed in ⅕ volume of lysis buffer (50 mM tris, pH 8.0, 50 mM EDTA, 0.1% Tween, 2 mg/ml lysozyme) and lysed for two hours on ice. The lysed cells were again centrifuged as before, and the supernatant containing the crude cell extract retained.

The 2,5-DKG reductase A protein was purified from the crude cell extract by chromatography on DEAE cellulose. DEAE cellulose (Whatman DE-52 brand) was pre-equilibrated with 25 mM tris, pH 7.0. A total of 5.0 ml of the gel was poured into a disposable plastic chromatography column, to which was applied the crude cell extract. After all of the extract had been bound to the column, the column was washed with two column volumes of 25 mM tris pH 7.0, then one volume of 25 mM tris pH 7.0 containing 0.3M NaCl, and finally the 2,5-DKG reductase A protein was eluted with 25 mM tris pH 7.0 containing 0.6M NaCl. The preparations were assayed for protein concentration by the bicinchoninic acid method (*Methods in Enzymology* 182:60–62 (1990)) and checked for purity by SDS polyacrylamide gel electrophoresis.

EXAMPLE 5

Kinetic Characterization Of The Wild-Type And The Mutant Q192R 2,5-DKG Reductase A The preparations of wild-type and mutant Q192R 2,5-DKG reductase A enzymes were characterized kinetically as to their ability to reduce the substrate 2,5-DKG to 2-KLG. Assays were done in 1 ml total volume of 50 mM tris, pH 7.0, containing 0.2 mM NADPH, a constant amount of enzyme (15–20 µg) and amounts of substrate varying from 2 to 14 mM. The assays were done at 25° C., and the rate of substrate reduction was measured spectrophotometrically by measuring the loss of absorbance at 340 nm wavelength (which is indicative of the oxidation of the cofactor NADPH to NADP+).

The data were analyzed according to the well-known Michaelis equation to determine the kinetic parameters Vmax and Km using the Enzfit software package (Biosoft, Cambridge, UK) on a Epson desktop computer. The wild-type 2,5-DKG reductase A had an apparent Vmax for the 2,5-DKG substrate of 7.8 µmoles per minute per milligram of protein, while the Q192R mutant had an apparent Vmax of 14.0, a 1.8 fold improvement. The Km or Michaelis constant of the wild-type enzyme was apparently 28 mM, while the Km of the Q192R mutant was apparently 21 mM for this substrate. This led to an apparent specificity constant (kcat/Km) of 140M$^{-1}$s$^{-1}$ for the wild-type enzyme and a specificity constant of 335M$^{-1}$s$^{-1}$ for the Q192R mutant, a 2.4 fold improvement.

EXAMPLE 6

Homology Model of 2.5-DKG Reductase A

A model of 2,5-DKG reductase variant A was built based on the coordinates of the aldose reductase:NADPH complex (Wilson et al., Science 257:81-84 (1992)), applying modeling methods (Greer, Methods in Enzymology 202:239-252 (1991), herein incorporated by reference; Bajorath et al., Protein Science 2:1798-1810 (1993), herein incorporated by reference), in which 'structurally conserved regions' (generally regions of secondary structure features like alpha helix and beta sheet, or regions of extensive sequence identity) are defined and held constant, to which 'loops' of variable amino acids are added later. The conformation of these loops are modeled by either conformational searches through the crystal structure data base, or by random conformation generation algorithms.

FIG. 6 shows the protein sequence alignment of 2,5-DKG reductases A and B with human aldose reductase; boxed residues show secondary structure features from the crystal structure of aldose reductase (Bruce et al., Biochem J. 299:805-811 (1994)(SEQ ID NO:2) (SEQ ID NO:3)). In this modeling, the main changes were: replacement of the long loop joining beta strand four and alpha helix four and beta strand seven and helix H1 with shorter loops, and modeling a new tail conformation to take into account the shorter tail of 2,5-DKG Reductase A. The remaining structure was held constant. Likely-looking structures for these loops were chosen from a number of possibilities generated by a random conformation generation program. The model was used to target a number of residues in the predicted active site of 2,5-DKG reductase for mutagenesis, and is also used in the following sections to illustrate the approximate locations of these mutants in the 2,5-DKG reductase barrel structure.

EXAMPLE 7

Construction of The F22Y Mutant of 2,5-DKG Reductase A

The homology model was used to determine structural differences around the substrate binding pocket that might be the basis of differences in the observed substrate turnover of the 2,5-DKG Reductase A and DKG Reductase B. In particular, the homology model was used to locate amino acids for replacement associated with the substrate binding pocket in the 2,5-DKG Reductase A that were less hydrophilic than the counterpart amino acid in the 2,5-DKG Reductase B.

Amino acid 22, appears to form part of the active site substrate specificity pocket in both the aldose reductase structure and in the 2,5-DKG Reductase A homology model. A phenylalanine is found in the 2,5-DKG Reductase A enzyme while a tyrosine occupies this position in the sequence of 2,5-DKG Reductase B. The extra hydroxyl moiety of tyrosine as compared to phenylalanine may contribute H-bonding capability to the active site region of the 2,5 DKG Reductase B enzyme.

The construction of these two mutants, F22Y and Y23F is as follows: four oligonucleotides were designed, two for mutagenesis and two for probing, as follows: A:F22Y.m= 5'-C GGG TAC GGC GTC TAC AAG GTG CCG CCG G-3'(SEQ ID NO:16), A:F22Y.p=5'-C GGC GTC TAC AAG GTG C-3'(SEQ ID NO:17), B:Y23F.m=5'-T GGG CTC GGC ACG TTC AAC CTG CGC GGC G-3'(SEQ ID NO:18), and B:Y23F.p=5'-C GGC ACG TTC AAC CTG C-3'(SEQ ID NO:19). The oligonucleotides with the suffix ".m" were kinased and used to mutate templates for the wild-type 2,5-DKG Reductase A and B genes with the Amersham kit, (templates are EcoRI-KpnI fragments of the genes for DKG reductases A and B in M13mp19). The steps in the mutagenesis reactions, the isolation and characterization of the mutants were essentially the same as outlined for construction of the Q192R mutant except the oligonucleotides with the suffix ".p" were used to isolate the mutants. The resulting F22Y mutant of 2,5-DKG Reductase A has a tyrosine at position 22 and the resulting Y23F mutant of 2,5-DKG Reductase B has a phenylalanine at position 23.

EXAMPLE 8

Figure 7:
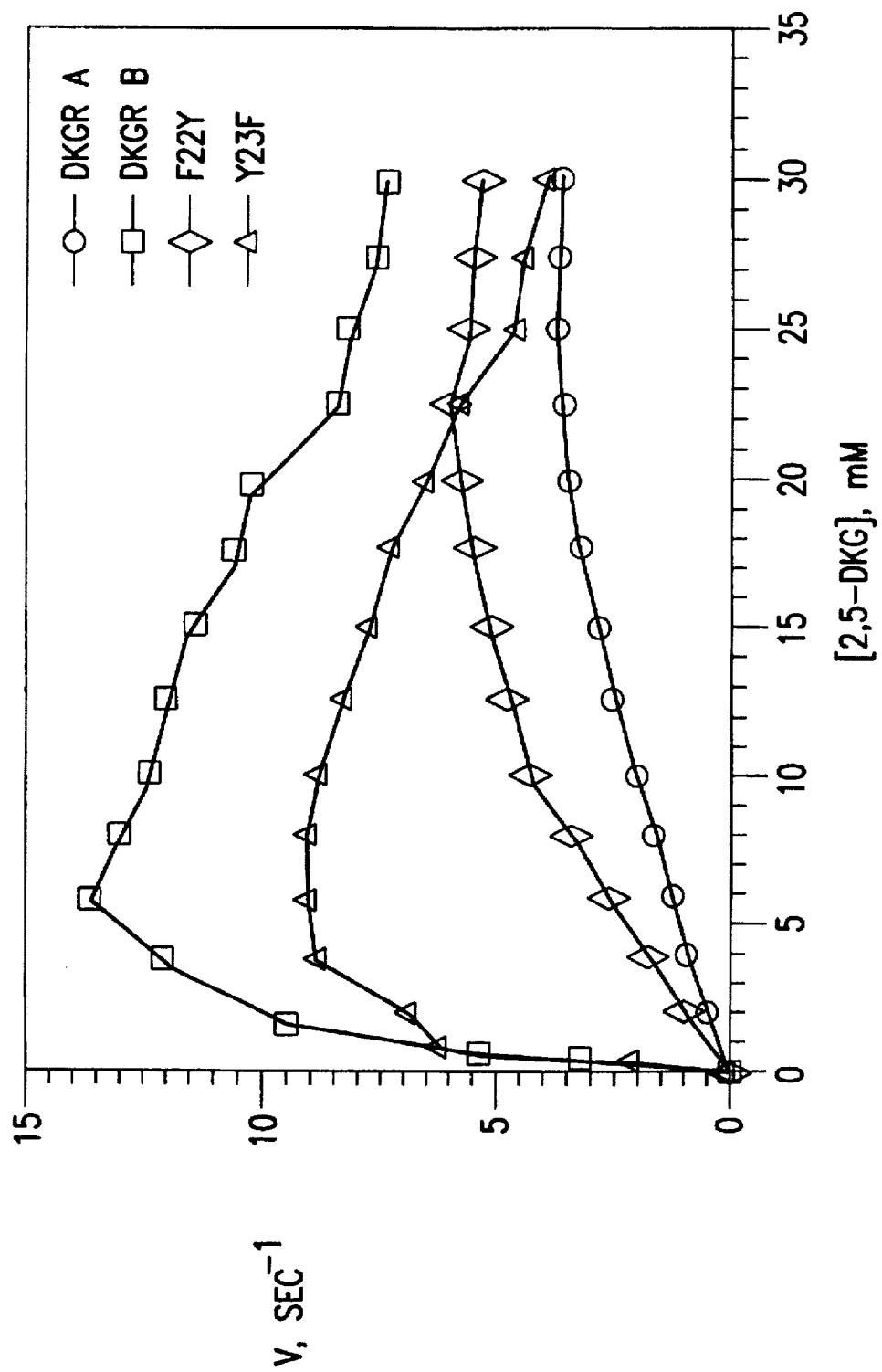
FIG. 7 shows the substrate kinetics of 2,5-DKG Reductase A mutant F22Y and 2,5-DKG Reductase B mutant Y23F compared with wild-type 2,5-DKG Reductases A and B.

Kinetic Characterization Of The F22Y Mutant of 2,5-DKG Reductase A and The Y23F Mutant 2,5-DKG Reductase B The kinetic characterization of 2,5-DKG Reductase A mutant F22Y and 2,5-DKG Reductase B mutant Y23F was carried out in essentially the same manner as in Example 5 except that in order to determine kinetic parameters for the NADPH-dependent reduction of 2,5-DKG by 2,5-DKG reductases, a series of reactions were done with constant saturating concentration of NADPH (200 µM) and varying concentrations of substrate from 0 to 30 mM. The 2,5-DKG Reductase A mutant F22Y shows significant and reproducible increased activity compared with the wild-type 2,5-DKG Reductase A (FIG. 7). The 2,5-DKG Reductase B mutant Y23F activity is lower than the wild-type 2,5-DKG Reductase B (FIG. 7). 2,5-DKG Reductase A mutant F22Y may also show an enhanced resistance to substrate inhibition compared to the wild-type 2,5-DKG Reductase B enzyme.

EXAMPLE 9

Construction of The I49N Mutant of 2,5-DKG Reductase A and The N50A Mutant of 2,5-DKG Reductase B Position 49, was selected for mutagenesis based on the proximity of this site to the substrate binding site in the homology model, and a pronounced hydrophobicity difference at that position in the 2,5-DKG Reductase A and B enzymes: 2,5-DKG Reductase A has an isoleucine at position 49, while 2,5-DKG Reductase B has an asparagine at position 50. Position 49 is found on a loop of amino acids joining beta strand 2 and alpha helix 2. Two mutants were constructed to test the effect of side chain mutations at this site: I49N, 2,5-DKG Reductase A mutant and 2,5-DKG Reductase B mutant N50A. Construction of these mutants were as follows: oligonucleotide sequences were as follows: A:I49N.m=5'-C GAC ACC GCG GCG AAC TAC GGA AAC GAA G -3'(SEQ ID NO:20), A:I49N.p=5'- C GCG GCG AAC TAC GGA A -3'(SEQ ID NO:21), B:N50A.m=5'-TC GAC ACG GCG GTG GCG TAC GAG AAC GAG AG -3'(SEQ ID NO:22), and B:N50A.p=5'- G GCG GTG GCG TAC GAG A -3'(SEQ ID NO:23). The steps in the mutagenesis reactions, the isolation and characterization of the mutants were essentially the same as outlined for construc-

21 tion of the F22Y mutant. The resulting I49N mutant of 2,5-DKG Reductase A has an asparagine at position 49 and the resulting N50A mutant of 2,5-DKG Reductase B has an alanine at position 50.

EXAMPLE 10

Figure 8:
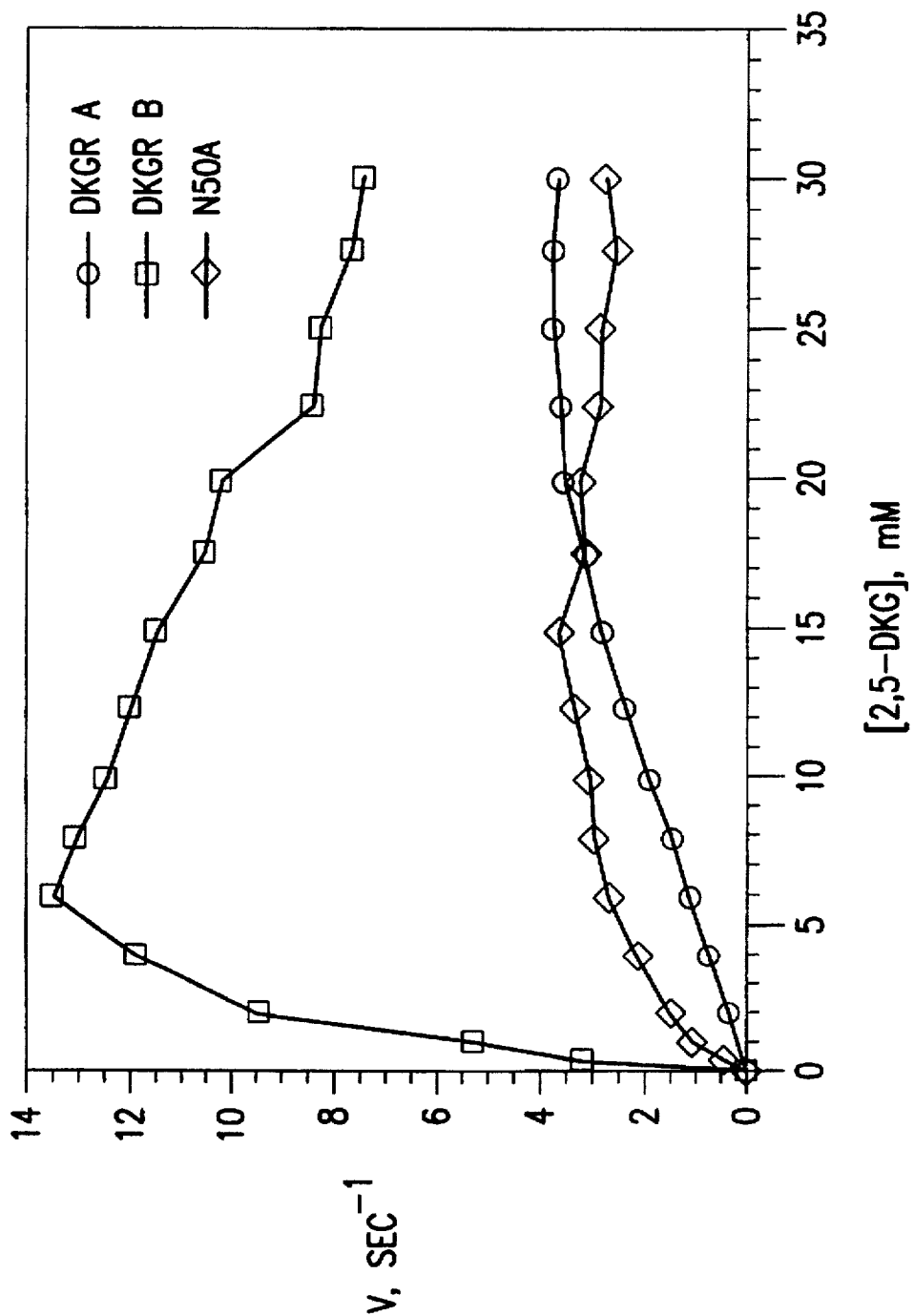
FIG. 8 shows the substrate kinetics of 2,5-DKG-Reductase B mutant N50A compared with wild-type 2,5-DKG Reductases A and B.

Kinetic Characterization Of The I49N Mutant of 2, 5-DKG Reductase A and N50A Mutant of 2,5 5-DKG Reductase B The kinetic characterization of 2,5-DKG Reductase A mutant I49N and 2,5-DKG Reductase B mutant N50A was carried out in essentially the same manner as in Example 5 except that in order to determine kinetic parameters for the NADPH-dependent reduction of 2,5-DKG by 2,5-DKG reductases, a series of reactions were done with constant saturating concentration of NADPH (200 µM) and varying concentrations of substrate from 0 to 30 mM. The 2,5-DKG Reductase A mutant I49N did not produce any detectable levels of recombinant protein in the host cell, probably due to structural instability. The 2,5-DKG Reductase B mutant N50A mutant expressed normally. Kinetic results for 2,5-DKG Reductase B mutant N50A are shown in FIG. 8. 2,5-DKG Reductase B mutant N50A does not exhibit substrate inhibition until substrate concentrations of greater than 15 mM. The wild-type 2,5-DKG Reductase B enzymes' activity declines after the addition of only 5 mM 2,5-DKG (FIG. 8).

EXAMPLE 11

Construction of 2,5-DKG Reductase A Mutants D278A, V277A, E276A, D275A, P274A, H273A, A272G, S271A, V270A, R269A, S267A, and D265A of 2,5-DKG Reductase A The technique of 'ala-scanning' was used to locate residues in the C-terminial of 2,5-DKG Reductase A (Cunningham and Wells, *Science* 204: 1081 (1989)), herein incorporated by reference. A total of 11 ala-scan mutants were constructed: D278A, V277A, E276A, D275A, P274A, H273A, S271A, V270A, R269A, S267A, and D265A based on the prediction that the region covered by these mutants was part of the enzymes' active site. In addition, the following non-ala scan mutant was generated: the 2,5-DKG Reductase A A272G mutant was produced by replacing alanine at position 272 with a glycine at that position. The 2,5-DKG Reductase mutants constructed using the following oligonucleotides: A:D278A:5'-GAT GAG GTC GCG TGA GGT ACC C-3'(SEQ ID NO24); A:V277A:5'CCC GAT GAG GCG GAC TGA GGT A-3'(SEQ ID NO:25); A:E276A:5'-CAC CCC GAT GCC GTC GAC TGA G-3' (SEQ ID NO:26); A:D275A:5'-GCA CAC CCC GCG GAG GTC GAC T-3'(SEQ ID NO:27); A:P274A:5'G AGC GCA CAC GCG GAT GAG GTC G-3'(SEQ ID NO:28); A:P274A:5'G AGC GCA CAC GCG GAT GAG GTC G-3'; A:H273A 5'-C GTG AGC GCA GCG CCC GAT GAG G-3'(SEQ ID NO:29); A:A272G:5'-CGC GTG AGC GGG CAC CCC GAT G-3'; A:S271A:5'-G GGT CGC GTG GCG GCA CAC CCC G-3'(SEQ ID NO:31); A:V270A:5'TCG GGT CGC GCG AGC GCA CAC C-3'(SEQ ID NO:32); A:R269A:5'C GGT TCG GGT GCG GTG AGC GCA C-3'(SEQ ID NO:33); A:S267A:5'G GGC GAC GGT GCC GGT CGC GTG A-3'(SEQ ID NO:34); A:D265A:5'GAT CCG GGC GCG GGT TCG GGT C-3'(SEQ ID NO:35). The steps in the mutagenesis reactions, the isolation and characterization of the mutants were essentially the same as outlined for construction of the Q192R mutant.

22

EXAMPLE 12

Figure 9:
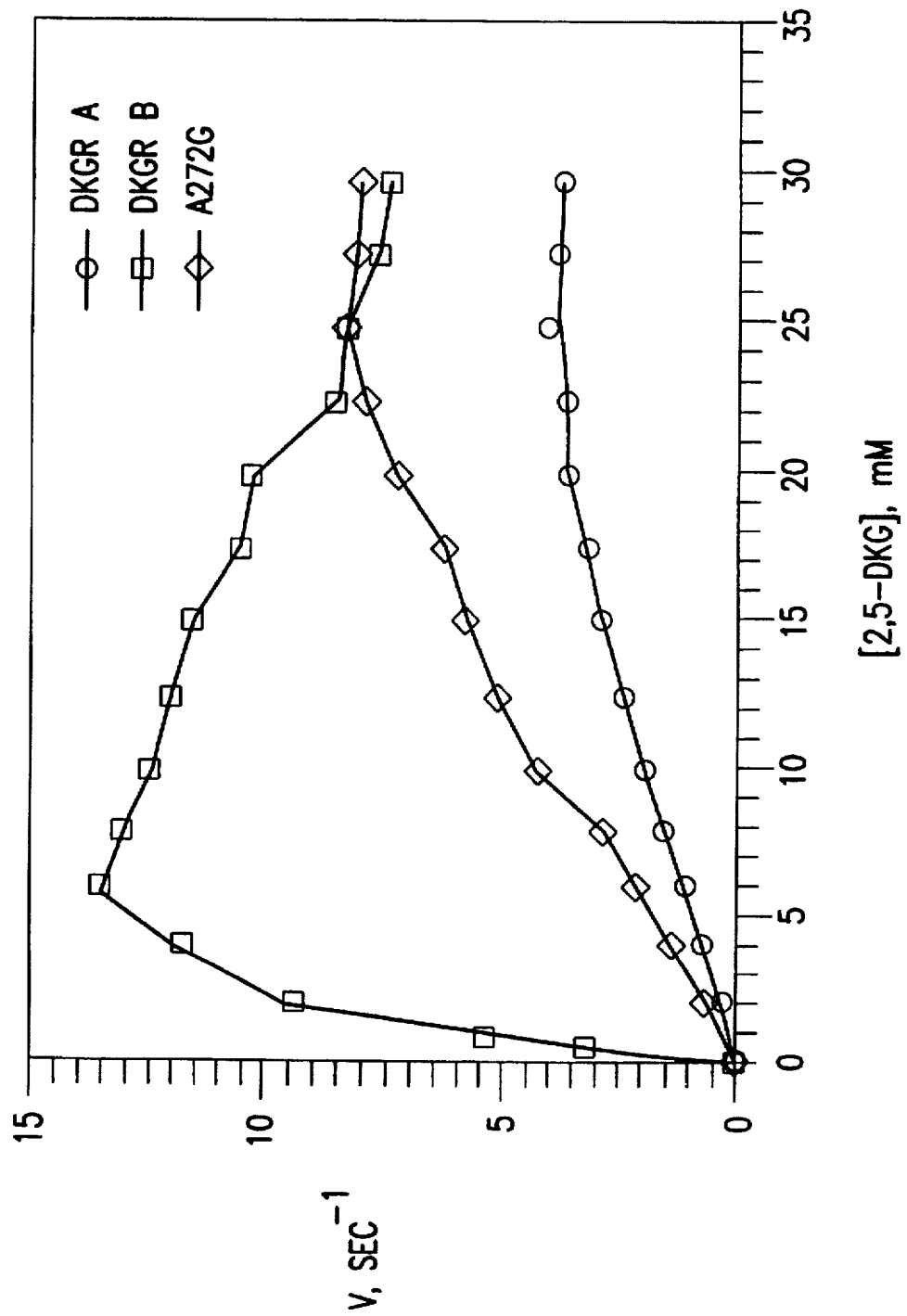
FIG. 9 shows the substrate kinetics of 2,5-DKG Reductase A mutant A272G compared with wild-type 2,5-DKG Reductases A and B.

Kinetic Characterization Of The 2,5-DKG Reductase Mutants D278A, V277A, E276A, D275A, P274A, H273A, A272G, S271A, V270A, R269A, S267A, and D265A of 2,5-DKG Reductase A A crude kinetic characterization of 2,5-DKG Reductase A mutants D278A, V277A, E276A, D275A, P274A, H273A, A272G, S271A, V270A, R269A, S267A, and D265A was carried out. One of these mutants, A272G, resulted in increased activity. 2–5-DKG Reductase A mutant A272G was characterized in essentially the same manner as in Example 5 except that in order to determine kinetic parameters for the NADPH-dependent reduction of 2,5-DKG by 2,5-DKG reductases, a series of reactions were done with constant saturating concentration of NADPH (200 µM) and varying concentrations of substrate from 0 to 30 mM. The mutant 2,5-DKG Reductase A mutant A272G showed significant and reproducible increase in activity over the wild-type A enzyme at all substrate concentrations, with only a slight indication of substrate inhibition in the range examined (See FIG. 9). The mutant exhibited an apparent Vmax of $21.44 \pm 4.10$ sec$^{-1}$ and an apparent Km of $42.61 \pm 12.13$ mM.

EXAMPLE 13

Construction of Double 2,5-DKG Reductase A Mutants F22Y/Q192R, Q192R/A272G, and F22Y/A272G Three 2,5-DKG Reductase A double mutants were constructed: F22Y/Q192R, Q192R/A272G, and F22Y/A272G. The constructs were as follows:

For the Q192R/A272G double mutant, plasmid ptrp1-35.A:Q192R was digested with EcoRI and BamHI to generate a 787 bp fragment containing the Q192R mutation. Plasmid ptrp1-35.A:A272G was digested BamHI and ClaI to generate a 708 bp fragment containing the A272G mutant. The two mutants were combined in a three way ligation with EcoRI and ClaI digested vector ptrp1-35.A to generate the double mutant ptrp1-35.A:Q192R/A272G. Mutants were verified by restriction digests to ensure that both of the expected fragments were in place. The resulting Q192R/A272G mutant of 2,5-DKG Reductase A has an arginine at position 192 and a glycine at position 272.

For the 2,5-DKG Reductase double mutant F22Y/A272G, an F22Y containing fragment of ~600 base pairs was prepared by EcoRI and ApaI digestion of plasmid ptrp1-35.A:F22Y. A fragment (~300 bp) bearing the mutation A272G was prepared by ApaI and KpnI digest of the plasmid ptrp1-35.A:A272G. The mutant was then combined in a three way ligation with EcoRI-KpnI digested ptrp1-35.A to yield plasmid ptrp1-35.A:F22Y/A272G. The resulting F22Y/A272G mutant of 2,5-DKG Reductase A has an tyrosine at position 22 and a glycine at position 272.

Mutant 2,5 DKG Reductase A F22Y/Q192R, was prepared by a similar strategy, however the oligonucleotide which directed the Q192R mutation removed the ApaI site so the construct was done through the XhoI site of the DKG reductase A gene. Plasmid ptrp1-35.A:F22Y was digested with EcoRI and XhoI, yielding a 435bp fragment containing the F22Y mutation.

In a second digest, ptrp1-35.A:Q192R was digested with XhoI and KpnI to yield a 400 bp fragment containing the Q192R mutation. These two fragments were combined in a three-way ligation with EcoRI and KpnI digested ptrp1-35.A to give plasmid ptrp1-35.A:F22Y/Q192R. The resulting F22Y/Q192R mutant of 2,5-DKG Reductase A has a tyrosine at position 22 and an arginine at position 192.

All three double mutants were confirmed by restriction mapping and direct sequencing to assure that the two proper mutations were in place.

EXAMPLE 14

Figure 10:
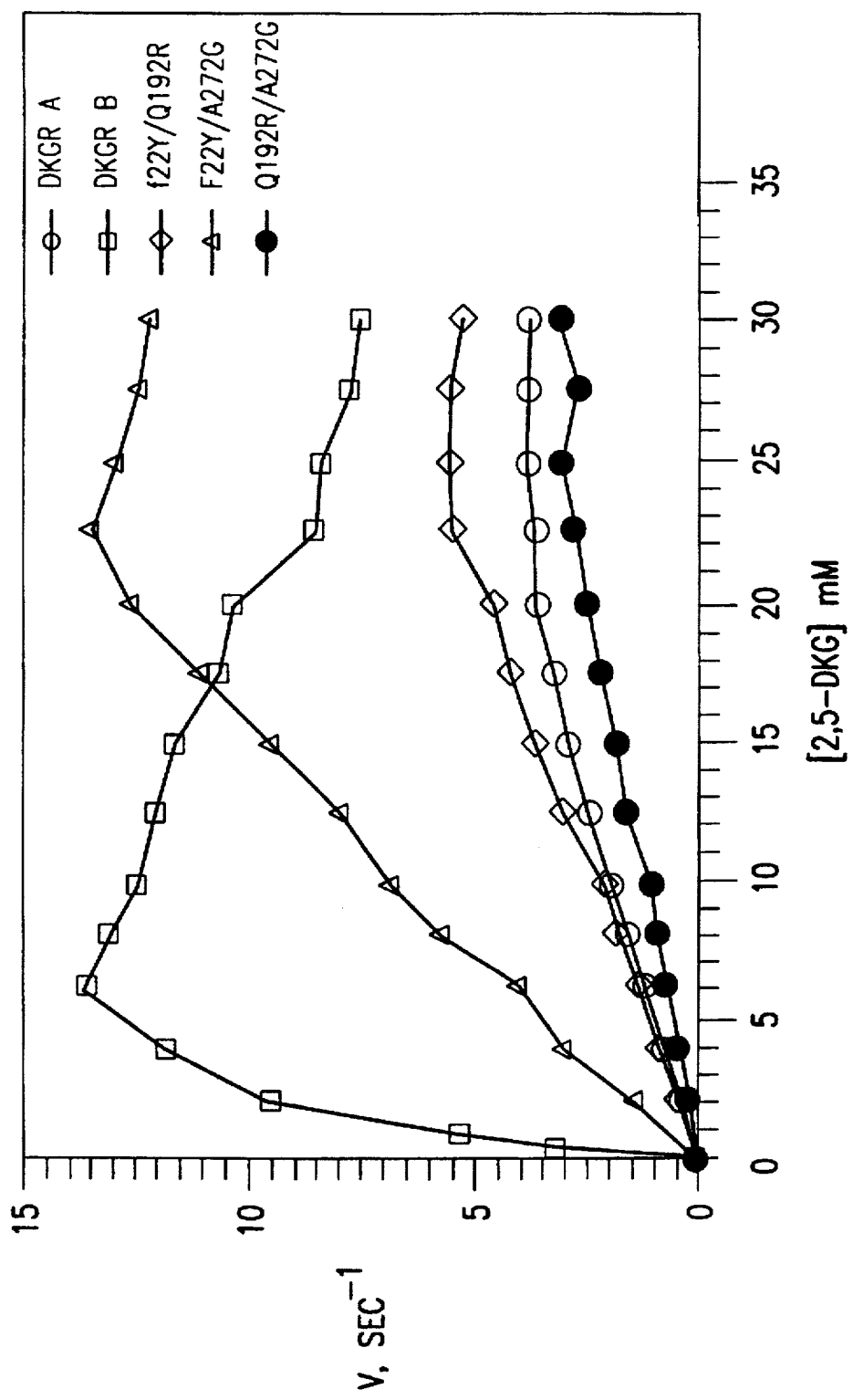
FIG. 10 shows the substrate kinetics of 2,5-DKG Reductase A mutant F22Y/Q192R, of 2,5-DKG Reductase A mutant F22Y/A272G and of 2,5-DKG Reductase A mutant Q192R/A272G compared with wild-type 2,5-DKG Reductases A and B.

Kinetic Characterization Of 2,5-DKG Reductase A Double Mutants F22Y/Q192R, Q192R/A272G, and F22Y/A272G The kinetic characterization of 2,5-DKG Reductase A double mutants F22Y/Q192R, Q192R/A272G, and F22Y/A272G was carried out in essentially the same manner as in Example 5 except that in order to determine kinetic parameters for the NADPH-dependent reduction of 2,5-DKG by 2,5-DKG reductases, a series of reactions were done with constant saturating concentration of NADPH (200 μM) and varying concentrations of substrate from 0 to 30 mM. The substrate kinetics for the double mutants are shown in FIG. 10. Double mutants that contain Q192R do not lead to increased activity. The catalytic activity of 2,5-DKG Reductase A mutant F22Y/Q192R is similar to that of the two parent mutants. The catalytic activity of 2,5-DKG Reductase A mutant Q192R/A272G is lower than wild-type DKG Reductase A. The 2,5-DKG Reductase A mutant F22Y/A272G double mutant has clear-cut additivity or even synergy over its two parent enzymes, and surpasses the activity of DKG reductase B at substrate concentrations greater than 17.5 mM. This double mutant also shows a substrate inhibition effect.

EXAMPLE 15

Cofactor Kinetic Characterization Of 2,5-DKG Reductase A Mutants F22Y, 5 Q192R, A272G, and F22Y/A272G The cofactor affinity of DKG reductase A F22Y, Q192R, A272G, and F22Y/A272G was determined by analysis of a series of reactions with constant substrate concentration and varying concentrations of NADPH.

Each series of reactions consisted of 50 mM bis-Tris pH 6.8, 10 mM 2,5-DKG, from 2.5 to 200 μM NADPH, and enzyme in a total volume of 1.0 ml.

Initial rate data for the reactions were fitted to the Michaelis-Menten equation by non-linear regression analysis as previously described to determine $KM,NADPH$. Results are shown in FIG. 11. Alterations to the Michaelis constant for NADPH in the mutants are not significant; the values are all within ±30% of the $K_{M,NADPH}$ of the wild-type enzyme and range from a high of 8.19 μM for 2,5-DKG Reductase A F22Y/A272G and a low of 4.92 μM for 2,5-DKG Reductase A A272G.

EXAMPLE 16

Mutant thermal stability of 2,5-DKG Reductase A Mutants F22Y, Q192R, A272G, and F22Y/A272G Thermal instability may be a critical characteristic of an enzyme that may limit its usefulness in an industrial process. The 2,5-DKG Reductase A mutants F22Y, Q192R, A272G, and F22Y/A272G with increased catalytic activity were subjected to circular dichroism analysis to determine what effects the mutations may have had on thermal stability.

Protein samples of 2,5-DKG reductase A and B and 2,5-DKG Reductase A mutants F22Y, Q192R, A272G, and F22Y/A272G were concentrated over Amicon YM-10 membranes, desalted into 10 mM phosphate buffer, pH 7.0 using a pre-packed G25 column (PD-10 from Pharmacia), and adjusted to 200 μg/ml final concentration for circular dichroism analysis. Samples were measured in an Aviv model 60DS circular dichroism spectrophotometer in a 1.0 mm cuvette. Measurements were corrected for buffer background. Raw ellipticity data (degrees) were converted to molar ellipticity values (degrees $M^{-1}$ $cm^{-1}$) by the relationship:

$$\text{molar ellipticity} = (100)(\text{ellipticity})/(C)(l)$$

where C is the molar concentration of the sample and l is the pathlength in centimeters. Proteins show minima at ~220 nm, which is indicative of alpha-helical content. Thermal denaturation was determined by monitoring loss of ellipticity at 220 nm as a function of temperature. Tms from the midpoint of the thermal denaturation curves are shown in FIG. 12.

EXAMPLE 17

Crystallization of 2,5-DKG Reductase A and 2,5-DKG Reductase A:NADPH Complex 2,5-DKG reductase A and B proteins were purified from large scale growths of A. cerinus carrying plasmids ptrp1-35.A and ptrp1-35.B. Fresh streaks of A. cerinus carrying plasmids ptrp1-35.A and ptrp1-35.B on LB plates containing antibiotics for selection (50 μg/ml ampicillin, 12.5 μg/ml tetracycline) were used to inoculate overnight culture of 10 mls liquid media (LB plus 50 μg/ml ampicillin and 12.5 μg/ml tetracycline). The following day the cultures were diluted 1:1000 into 6 liters fresh media and grown at 28° C. for 24 hours. Cells were harvested by centrifugation (GSA rotor, 9000 rpm for 20 minutes), and cell pellets stored at −70° C. until use. The following purification procedure was carried out in its entirety either on ice or at 4° C. The cells were thawed and resuspended in ⅕ volume (200 mls per liter original culture) of ice-cold lysis buffer (50 mM Tris pH 8.0, 25 mM EDTA, 0.1 % Tween 80, 1.0 mg/ml lysozyme) and allowed to lyse on ice for 2 hours. The lysate was centrifuged at 9000 rpm in a GSA rotor for 30 minutes, and the supernatant fraction containing soluble 2,5-DKG reductase retained as the 'crude lysate' fraction. To the crude lysate was added 50 ml bed volume of Amicon RedA dye affinity matrix, previously equilibrated with buffer A (25 mM Tris pH 7.5), that was allowed to bind on ice with occasional stirring. After binding, the RedA gel was allowed to settle out of suspension, and then washed two times with 500 mls buffer A. After the second wash, the gel was resuspended in a small volume buffer A, poured into a Biorad Econocolumn (2.5 cm dia×25 cm), washed with 100 mls buffer A, and step eluted with 100 mls buffer A plus 0.5 mM NADPH. The 100 ml eluate ('RedA pool') was bound to a 40 ml DEAE cellulose column (Whatman DE-52), and then washed with 50 ml buffer A, and eluted with a 400 ml linear salt gradient consisting of 200 mls buffer A and 200 mls buffer A plus 1.0M NaCl. The gradient was pumped at a flow rate of 220 ml/hr and 5.5 ml fractions collected, and assayed by $A_{280}$. Two major peaks of $A_{280}$ absorbance are observed, the first consisting mostly of NADPH and contaminating proteins while the second peak eluting at ~0.4M NaCl contains the 2,5-DKG reductase. The second peak was pooled ('DE-52 pool') and gel filtered over a Sephadex G-75 column in buffer A (2.5 cm dia.×66 cm, column volume= ~320 ml) to remove salt and any residual NADPH. Fractions are were collected and assayed by $A_{280}$. A single peak of $A_{280}$ absorbing material corresponding to ~30,000 daltons molecular weight was observed. Peak fractions from the G-75 column were pooled ('G-75 pool') and used for further characterization. SDS-PAGE gel analysis of the fractions show that the material is homogeneous after purification. UV absorbance scans confirm that no detectable NADPH (by A340 absorbance) remains in the final product.

Cell lysates of *A. cerinus* show activity in the DKG reductase assay even from pBR322 transformed cells, however as this assay only measures NADPH oxidation, the observed reduction could be do to reduction of 2,5-DKG at either carbonyl 2 or 5, and with either stereochemistry. Control experiments with pBR322 lysates show that the background reductase activity is completely removed by this purification protocol. Yields from this purification protocol are typically 2–4 mg protein per liter of cells.

The protein DKG reductase A was dialyzed in deionized water (3 liters) and concentrated under vacuum on YM-10 membranes from Amicon to 11.5 mg/ml for DKG reductase A and 6.9 mg/ml for DKG reductase B. Crystallizations were carried out at 6.5:1 and 11:1 NADPH:protein ratios for DKG reductase A and B respectively. Crystals formed as needles of ~0.6 mm in length and ~0.01 mm thick for the 2,5-DKG Reductase A:NADPH complex under conditions corresponding to Jancarik and Kim's solution 35 (0.8M sodium phosphate monobasic, 0.8M potassium phosphate monobasic, 100 mM Hepes buffer pH 7.5). Identical crystals also formed in the absence of NADPH.

The needles were seen to grow in the other two dimensions, giving rise to 'blades' and 'columns' as follows.

A single crystal of approximate dimensions of ~0.5 mm×0.5 mm×2 mm was grown from a 6 μl hanging drop consisting of 3 μl protein plus NADPH (16 mg/ml protein, 3:1 molar ratio of NADPH to enzyme) plus 3 μl of precipitating solution (2.0M Na, K phosphate, pH 6.5) suspended over an 800 μl reservoir of the same precipitant. The crystal was grown at room temperature.

EXAMPLE 18

X-Ray Diffraction of 2,5-DKG Reductase A:NADPH

Figure 13:
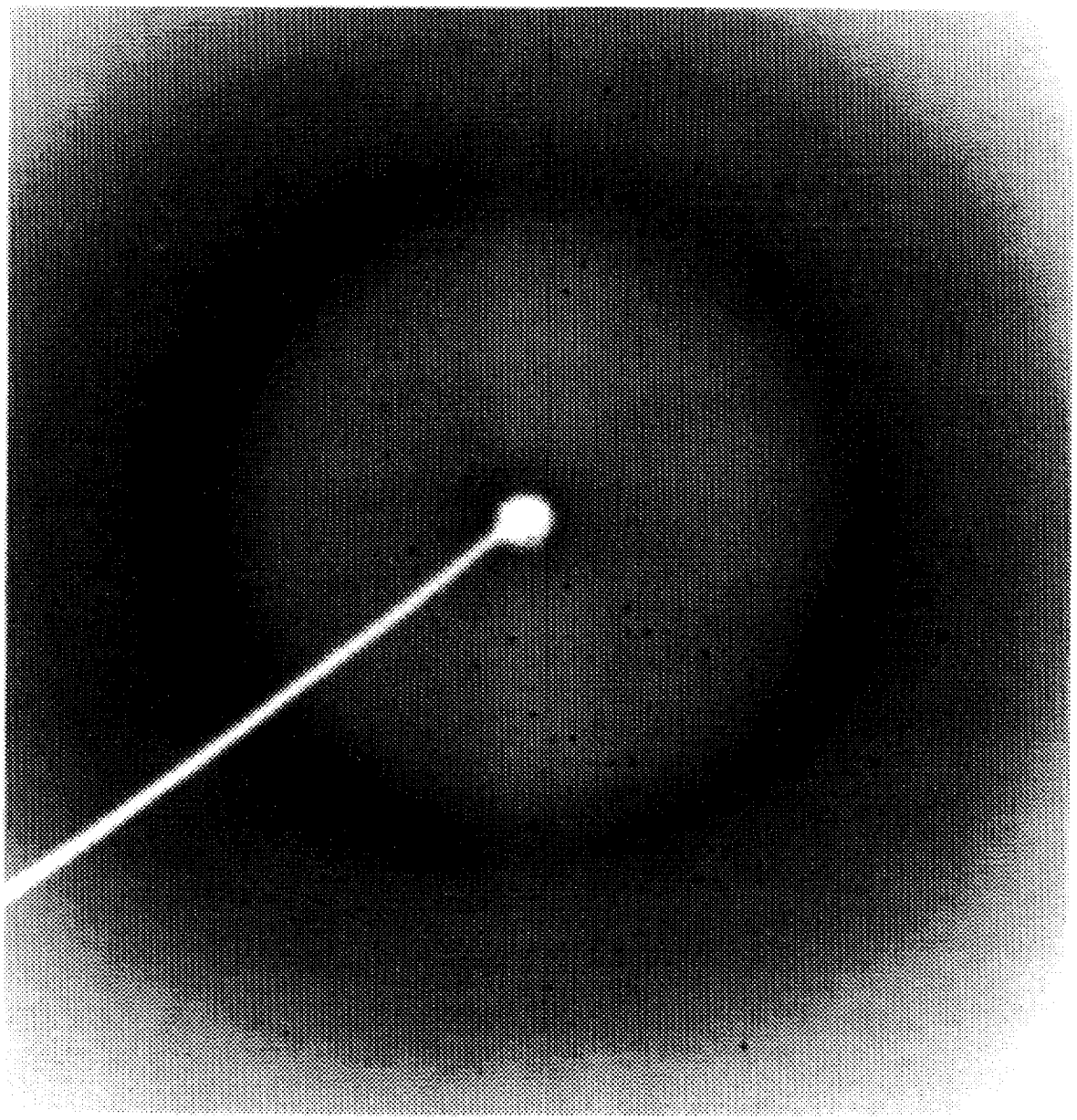
FIG. 13 shows a diffraction pattern from a crystal of the 2,5,-DKG Reductase A:NADPH complex.

A single crystal of 2,5-DKG Reductase A:NADPH with approximate dimensions 0.5×0.5×2 mm was isolated for diffraction analysis and mounted in a 0.7 mm quartz capillary tube. Diffraction data were collected at 5° C. with R-axis 2 instrument using copper K alpha radiation (1.5418 angstrom wavelength), at a distance of 100 centimeters to the image. FIG. 13 shows an oscillation picture (2 degrees oscillation) with exposure time of 40 minutes. Crystals diffracted to 2.9 Å with unit cell parameters of a=42.54 Å, b=55.79 Å, c=74.15 Å; α=β=γ=90.

As will be apparent to those skilled in the art in which the invention is addressed, the present invention may be embodied in forms other than those specifically disclosed above without departing from the spirit or essential characteristics of the invention. The particular embodiments of the present invention described above, are, therefore, to be considered in all respects as illustrative and not restrictive. The scope of the present invention is as set forth in the appended claims rather than being limited to the examples contained in the foregoing description.

---

What is claimed is:

1. A mutant form of a 2,5 diketo-gluconic acid reductase, 2,5-DKG reductase A, having improved ability to convert 2,5-DKG into 2-KLG, wherein said mutant form differs in amino acid sequence from SEQ ID NO:1, a wild-type form of a 2,5-DKG reductase enzyme, by:

(A) the replacement of an amino acid residue selected from the group consisting of residues 21, 22, 23, 24, 25, 46, 47, 48, 49, 50, 51, 52, 164, 169, 170, 199, 200, and 235 of said wild-type enzyme; or (B) the deletion of an amino acid residue selected from the group consisting of residues 21, 22, 23, 24, 25, 46, 47, 48, 49, 50, 51, 52, 164, 169, 170, 199, 200, and 235 of said wild-type enzyme.

2. The mutant according to claim 1, having a tyrosine at position 22.

3. The mutant according to claim 1, having a serine, threonine, histidine, glutamine, asparagine, or tryptophan at position 22.

4. A mutant form of 2,5-DKG reductase A according to claim 1 having a glycine at position 272.

5. The mutant according to claim 1, having amino acid substitutions in positions 22 and 272.

6. The mutant according to claim 1, having a tyrosine at position 22 and a glycine at position 272.

7. A mutant form of a 2,5-DKG reductase A according to claim 1, wherein said mutant has mutations in the amino acid sequence at residues 22 and 192.

8. A mutant form of a 2,5-DKG reductase A wherein said mutant differs in amino acid sequence from a wild-type form of a 2,5-DKG reductase A according to claim 1 by:

(A) the replacement of an amino acid selected from the group consisting of residues 21, 22, 23, 24 and 25 of said wild-type enzyme or (B) the deletion of an amino acid residue selected from the group consisting of residues 21, 22, 23, 24 and 25 of said wild-type enzyme.

9. A mutant form of a 2,5-DKG reductase A according to claim 1 wherein said mutant differs in amino acid sequence from a wild-type form of a 2,5-DKG reductase enzyme by:

(A) the replacement of an amino acid selected from the group consisting of residues 46, 47, 48, 49, 50, 51, and 52 of said wild-type enzyme or (B) the deletion of an amino acid residue selected from the group consisting of residues 46, 47, 48, 49, 50, 51, and 52 of said wild-type enzyme.

10. A mutant form of a 2,5-DKG reductase A according to claim 1 wherein said mutant differs in amino acid sequence from a wild-type form of a 2,5-DKG reductase enzyme by:

(A) the replacement of an amino acid selected from the group consisting of residues 164, 169, and 170 of said wild-type enzyme or (B) the deletion of an amino acid residue selected from the group consisting of residues 164, 169, and 170 of said wild-type enzyme.

11. A mutant form of a 2,5-DKG reductase A according to claim 1 wherein said mutant differs in amino acid sequence from a wild-type form of a 2,5-DKG reductase enzyme by:

(A) the replacement of an amino acid selected from the group consisting of residues 199 and 200 of said wild-type enzyme or (B) the deletion of an amino acid residue selected from the group consisting of residues 199 and 200 of said wild-type enzyme.

12. A mutant form of a 2,5-DKG reductase A according to claim 1 wherein said mutant differs in amino acid sequence from a wild-type form of a 2,5-DKG reductase enzyme by:

(A) the replacement of an amino acid at residue 235 of said wild-type enzyme or (B) the deletion of an amino acid at residue 235 of said wild-type enzyme.

* * * * *